US006493566B1

United States Patent
Ruchti et al.

(10) Patent No.: US 6,493,566 B1
(45) Date of Patent: Dec. 10, 2002

(54) CLASSIFICATION SYSTEM FOR SEX DETERMINATION AND TISSUE CHARACTERIZATION

(75) Inventors: Timothy L. Ruchti, Gilbert, AZ (US); Stephen F. Malin, Glendale, CA (US); Suresh Thennadil, Tempe, AZ (US); Jessica Rennert, Scottsdale, AZ (US); Glenn Aaron Kees, Tempe, AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 0 days.

(21) Appl. No.: 09/487,733

(22) Filed: Jan. 19, 2000

Related U.S. Application Data

(63) Continuation-in-part of application No. 09/359,191, filed on Jul. 22, 1999.
(60) Provisional application No. 60/116,883, filed on Jan. 22, 1999.

(51) Int. Cl.[7] .............................................. A61B 5/100
(52) U.S. Cl. ........................ 600/310; 600/309; 600/322
(58) Field of Search ................................ 209/576–590; 600/300, 309, 310, 322; 356/39–41; 250/339.01–339.09, 339.12

(56) References Cited

U.S. PATENT DOCUMENTS

| | | | | | |
|---|---|---|---|---|---|
| 3,859,522 A | * | 1/1975 | Cuthbert | .................. | 250/223 R |
| 5,606,164 A | * | 2/1997 | Price et al. | ............. | 250/339.09 |
| 5,880,464 A | * | 3/1999 | Vrionis | ....................... | 250/230 |

OTHER PUBLICATIONS

Bezdek, J. and S. Pal, *Fuzzy Models for Pattern Recognition: Methods that Search for Structures in Data*, IEEE Press.

Bliznak, J. and T. Staple, *Roentgenographic Measurement of Skin Thickness in Normal Individuals*, 1975, Mallinckrodt Institute of Radiology.

Cheng et al., *Process for sexing cow embryos*, Mar. 1999, U.S. Pat. No. 5,876,942.

Duda, R. and P. Hart, *Pattern Classification and Scene Analysis*, 1973, Library of Congress.

Durnin, J. and M. Rahaman, The assessment of the amount of fat in the human body from measurements of skinfold thickness, 1967, British Journal.

Frasch et al. *Procedure for the sex determination of embryos in mammals especially applied to bovine embryos*, Nov. 1996, U.S. Pat. No. 5,578,449.

Geladi, P., D. MacDougall, and H. Martens, Linearization and Scatter–Correction for Near–Infrared Reflectance Spectra of Meat, Jun. 1984, Applied Spectroscopy, vol. 39, No. 3.

Heyward, V. and L. Stolarczyk, *Applied Body Composition Assessment*, 1996, Library of Congress.

Johnston, F., *Relationships Between Body Composition and Anthropometry*, 1982. Wayne State University Press.

(List continued on next page.)

*Primary Examiner*—Eric F. Winakur
*Assistant Examiner*—Matthew Kremer
(74) *Attorney, Agent, or Firm*—Michael A. Glenn; Christopher Peil

(57) ABSTRACT

Instrumentation and procedures for noninvasively determining the sex of human and animal subjects in vivo have been developed based on the irradiation of skin tissue with near infrared light. The method of sex determination provides additional information about primary sources of systematic tissue variability, namely, the thickness of the dermis and the subcutaneous fat. Categorization of subjects on the basis of the determination is therefore suitable for further spectral analysis and the measurement of biological and chemical compounds, such as blood analytes.

33 Claims, 19 Drawing Sheets

OTHER PUBLICATIONS

Keller, J., M. Gray, and J. Givens, A Fuzzy K–Nearest Neighborhood Algorithm, 1985, IEEE.

Khalil. O., Spectroscopic and Clinical Aspects on Noninvasive Glucose Measurements, 1999, Clinical Chemistry 45, No. 2.

Kowalski, B., Chemometrics: Theory and Application, Sep. 1976, ACS Symposium Society.

Martens, H. and T. Naes, *Multivariate Calibration*, 1974, John Wiley & Sons.

Miyakawa et al, *Fish sex discrimination equipment and method*, May 1991, U.S. Pat. No. 5,013,906.

Pao, Y., *Adaptive Pattern Recognition and Neural Networks*, 1989, Library of Congress.

Roe. J. and B. Smoller, Bloodless Glucose Measurements, 1998, Critical Reviews in Therapeutic Drug Carrier Systems, 15(3).

Savitzky, A. and M. Golay, Smoothing and Differentiation of Data by Simplified Least Squares Procedures, 1964, Analytical Chemistry.

Shuster, S., M. Black, and E. McVitie, The influence of age and sex on skin thickness, skin collagan, and density, 1975, British Journal of Dermatology.

Suzuki, K., *Apparatus for determining the sex of a chick*, Nov. 1983, U.S. Pat. No. 4,417,663.

Tan. C., B. Statham, R. Marks, and P. Payne, Skin thickness measured by pulsed ultrasound: its reproducibility, validation, and variability, 1982, British Journal of Dermatology.

Wanke, R., E. Wolf, W. Hermann, S. Folger, T. Buchmuller, and G. Brem, The GH–Transgenic Mouse as an Experimental Model for Growth Research: Clinical and Pathological Studies, 1992, *Vetrinary Pathology and Molecular Animal Breeding*.

* cited by examiner

CLASSIFICATION SYSTEM FOR SEX DETERMINATION AND TISSUE CHARACTERIZATION

This application is a continuation-in-part of S. Malin, T. Ruchti, An Intelligent System for Noninvasive Blood Analyte Prediction, U.S. patent application Ser. No. 09/359,191, filed Jul. 22, 1999, which claims priority from Provisional Patent Application No. 60/116,883, filed Jan. 22, 1999.

BACKGROUND OF THE INVENTION

1. Technical Field

The invention relates to the determination of the sex of both human and animal subjects. More particularly, the invention relates to the instrumentation and method by which the sex and general tissue parameters of human and animal subjects can be determined noninvasively.

2. Description of the Prior Art

Near infrared (NIR) tissue spectroscopy is a promising noninvasive technology which bases measurements on the irradiation of a tissue site with NIR energy in the 700–2500 nanometer wavelength range. The energy is focused onto an area of the skin and propagates according to the scattering and absorption properties of the skin tissue. Therefore, the reflected or transmitted energy that escapes and is detected provides information about the tissue volume that is encountered.

Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat, and blood analytes absorb light proportionally to their concentration through unique absorption profiles or signatures. The measurement of tissue properties, characteristics or composition is based on detecting the magnitude of light attenuation resulting from its respective scattering and/or absorption properties.

Blood Analyte Measurement

While noninvasive measurement of blood analytes, such as blood glucose concentration, has been pursued through NIR spectroscopy, the reported success and product viability has been limited by the lack of a system for compensating for structural variations between individuals that produce dramatic changes in the optical properties of the tissue sample (for example see O. Khalil, *Spectroscopic and clinical aspects of non-invasive glucose measurements*, Clin. Chem., vol. 45, pp. 165–77 (1999) or J. Roe, B. Smoller. *Bloodless Glucose Measurements*, Critical Reviews in Therapeutic Drug Carrier Systems, vol. 15, no. 3, pp. 199–241 (1998). These differences are largely anatomical and provide distinct systematic spectral absorbance features or patterns that can be related directly to specific characteristics such as dermal thickness, protein levels, and percent body fat. While the absorbance features are repeatable by subject, over a population of subjects they produce confounding nonlinear spectral variation. Therefore, differences between subjects are a significant obstacle to the noninvasive measurement of blood analytes through NIR spectral absorbance.

An apparatus and procedure for substantially reducing this problem by the classifying subjects according to major skin tissue characteristics prior to blood analyte prediction is described in S. Malin, T. Ruchti, An Intelligent System for Noninvasive Blood Analyte Prediction, U.S. patent application Ser. No. 09/359,191, filed Jul. 22, 1999. The selected characteristics are representative of the actual tissue volume irradiated and the amount of the target analyte that is sampled. By grouping individuals according to the similarity of spectral characteristics representing the tissue structure, the nonlinear variation described above is reduced and prediction of blood analytes becomes more accurate.

In human subjects, significant differences related to sex have been discovered in the skin tissue. These differences include the thickness of the dermis (see: C. Tan, B. Statham, R. Marks, P. Payne, *Skin thickness measurement by pulsed ultrasound: its reproducibility, validation and variability*, British Journal of Dermatology, vol. 106, pp. 657–667, (1982) and J. Bliznak, T. Staple, *Roentgenographic measurement of skin thickness in normal individuals*, Radiology, vol. 116, pp. 55–60 (July 1975)), the amount of fat in subcutaneous tissue (see J. Durnin, M. Rahaman, *The assessment of the amount of fat in the human body from measurements of skinfold thickness*, British Journal of Nutrition, vol. 21 (1967) and F. Johnston, *Relationships between body composition and anthropometry*, Human Biology, Vol. 54, No. 2, pp. 221–245 (May 1982)) and skin collagen and density (see S. Shuster, M. Black, E. McVitie, *The influence of age and sex on skin thickness, skin collagen and density*, British Journal of Dermatology, vol. 93 (1975)). The determination of subject sex therefore provides an important indication of large systematic differences in the tissue structure and composition.

Therefore, an automated method for the determination of the subject's sex provides valuable information relevant to subject classification and determination of key tissue properties for blood analyte measurement.

Sex Determination of Animals

The determination of the sex of animal species has commercial benefit in certain industries due to the replacement of a human expert by an accurate and automated noninvasive device (see T. Miyakawa, O. Kato, Y. Koike, K. Matsunami, N. Sekiya, Fish sex discrimination equipment and method, U.S. Pat. No. 5,013,906 (May 7, 1991); K. Suzuki, Apparatus for determining the sex of a chick, U.S. Pat. No. 4,417,663 (Nov. 29, 1983); A. Frasch, R. Ugalde, Procedure for the sex determination of embryos in mammals especially applied to bovine embryos, U.S. Pat. No. 5,578,449 (Nov. 26, 1996); and W. Cheng, C. Chen, C. Hu, C. Wang, K. Choo, Process for sexing cow embryos, U.S. Pat. No. 5,876,942 (Mar. 2, 1999)). In Miyakawa et al supra. the sex of a fish is determined by examining the color of the genital gland area through visible light. In Suzuki et al supra. the sex of a chick is determined by examining the color of the anal region through the use of visible light. In Frasch et al and Cheng et al supra. methods for sexing cow embryos are detailed through a complex method of polymerase chain reactions. These methods are not extendable to human subjects or other mammals due to gross anatomical differences. Further, the methods are limited because they involve either the automated color detection of a particular often unexposed region of the animal or rely on measurements that are invasive or semi-invasive. Finally, none of the methods listed above use a near-infrared technology that penetrates the tissue to measure its internal properties. Therefore, a device for sex determination of animals needs to be developed that is accurate, noninvasive, automated, and general.

Body Composition Determination

The automated and noninvasive determination of sex provides beneficial information related to the body composition of the subject. For example, in the determination of the lean-body mass of humans, the knowledge of the subject's sex is required prior to analysis of other anthropometric measurements (see V. Heyward, L. Stolarczyk,. *Applied Body Composition Assessment*, Human Kinetics, Champaign, Ill. (1996)). An automated and noninvasive device for sex determination provides a critical component for a fully automated method of body composition analysis.

It would be advantageous to provide a novel apparatus and related procedures for sex determination of human and animal subjects through NIR tissue spectroscopy that has particular benefit in several areas, including blood analyte prediction, animal sex determination, and body composition evaluation.

SUMMARY OF THE INVENTION

The invention herein provides a novel method of sex determination for animals and humans based on near-infrared measurements of the skin tissue. In addition, the invention provides fundamental information regarding gross tissue characteristics and can be used for determination of systematic and relative differences in the thickness of the dermis and the amount of subcutaneous fat at the measurement site.

The invention is a method for non-invasively determining the sex of human or animal subjects. The method uses a spectroscopic apparatus in conjunction with an optical interface to measure tissue properties and characteristics that are manifested spectrally and that vary systematically according to the subject's sex.

The procedure for sex determination involves a calibration model that is empirically derived from a set of exemplary samples consisting of NIR tissue measurements and the actual sex of a population of subjects. The model is a set of parameters and computer generated code that is implemented to predict the subject's sex. The prediction consists of a discrete sex determination (male or female) and one or more relative property magnitudes that reveal information regarding the tissue properties of the sampled tissue volume. These properties include but are not limited to the thickness of the dermis, the collagen content, the skin density, and the amount of subcutaneous fat at the measurement site.

DETAILED DESCRIPTION OF THE INVENTION

The invention provides an apparatus for measuring the infrared absorption by tissue irradiated with near-infrared energy and a procedure of determining the subject's sex.

Apparatus

Figure 1:
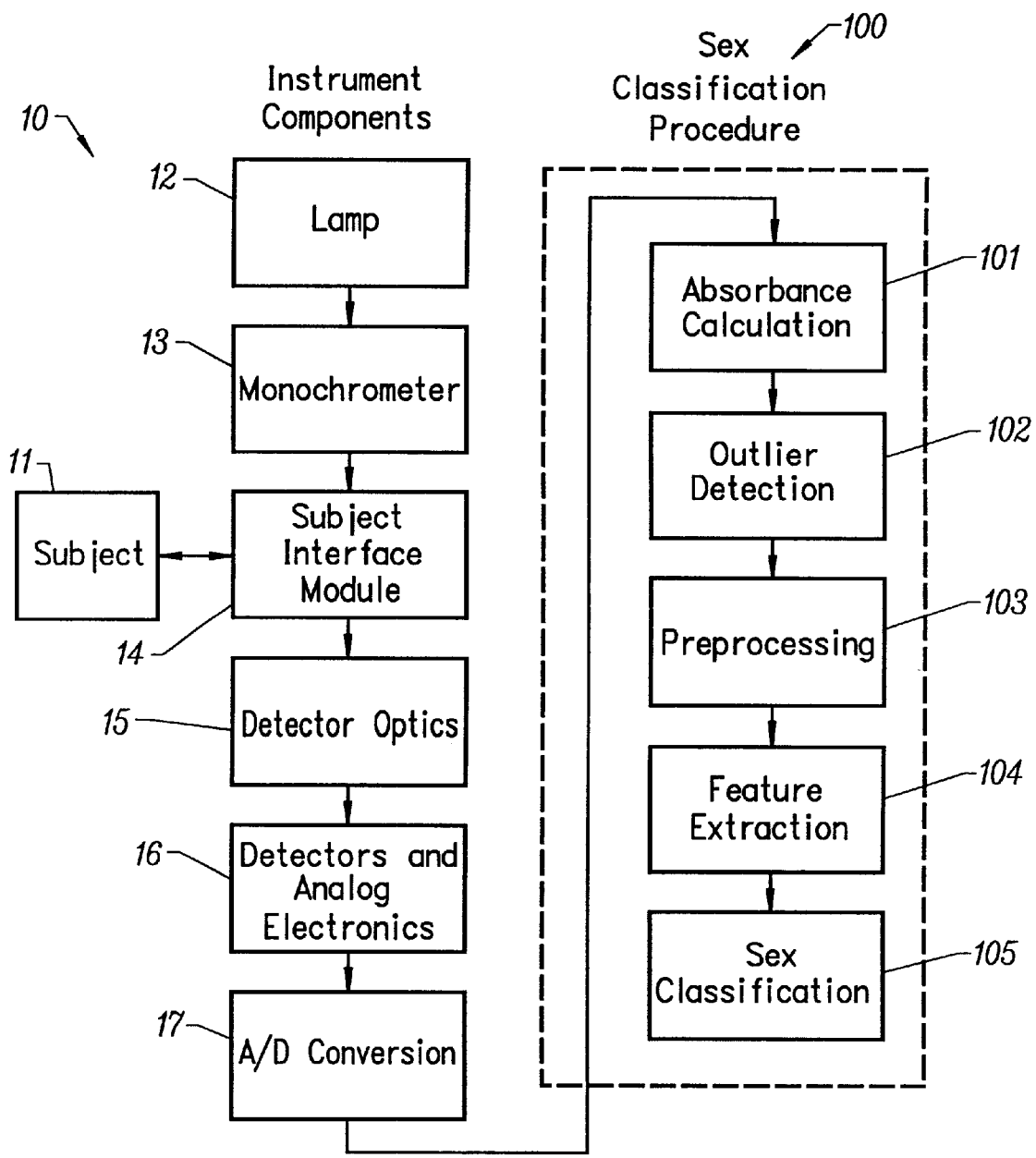
FIG. 1 is a block diagram of a sex classification instrument and sex classification procedure according to the invention.

A block diagram of the integrated system is shown in FIG. 1. The apparatus includes an energy source, a sensor element, an interface to the subject, a wavelength selection device and an analyzer. The source generates and transmits near-infrared energy in the wavelength range 700–2500 nanometers and consists of a device, such as an LED array or a quartz halogen lamp 12. The sensing elements include detector optics 15 and detectors 16 which are responsive to the targeted wavelengths. The method of wavelength separation includes a monochrometer 13, an interferometer or successive illumination through the elements of an LED array. The interface 14 to the subject 11 is a method of transmitting energy from the source to the target skin tissue measurement site and includes, for example a light pipe, fiber-optics, a lens system or a light directing mirror system. Energy is collected from the surrounding tissue areas in reflectance mode at an optimally determined distance(s) through the use of starring detectors or fiber optic probes. Alternately, energy is collected in a transmission mode through a skin flap, ear lobe, finger or other extremity. The collected light is converted to a voltage and sampled through an analog-to-digital converter 17 for analysis on a microprocessor based system.

In one embodiment a group of LEDs are employed to transmit energy at pre-selected wavelengths to the skin and radially surround a single detection element at specific distances. The LEDs are alternately energized and the detected energy of each LED that is reflected or transmitted through the skin is used to form one spectrum. While numerous distances are possible, the preferred implementation has a minimum of 1 mm and maximum of 3 mm edge-to-edge distance between the LEDs and the point of detection. The set of wavelengths include 1070, 1220, 1250, 1330, 1380, 1430 nanometers and/or 1550, 1560, 1670 and 1800 nanometers. Coupling of the illumination and detection elements is accomplished through starring optics and a lens system. One skilled in the art can appreciate that other coupling methods are also applicable including fiber optics given the criterion for the distance between the point of illumination and detection.

In the preferred embodiment of the invention, the instrument employs a quartz halogen lamp, a monochrometer, and InGaAs detectors. The detected intensity from the sample is converted to a voltage through analog electronics and digitized through a 16-bit A/D converter 17. The spectrum is passed to the sex classification procedure 100 for processing. First, the absorbance is calculated (101) on the basis of the detected light through $-\log(R/R_o)$ where R is the reflected light and $R_o$ is the light incident on the sample determined by scanning a reference standard. Subsequent processing steps, described below, result in either a sex determination or a message indicating an invalid scan.

Alternately, the measurement can be accomplished with existing NIR spectrometers that are commercially available, including a Perstorp Analytical NIRS 5000 spectrometer or a Nicolet Magna-IR 760 spectrometer. In addition, the measurement can be made by collecting reflected light off the surface of the skin or light transmitted through a portion of the skin, such as the finger or the ear lobe. Further, the use of reflectance or transmittance can replace the preferred absorbance measurement.

General Sex Classification Procedure

The general procedure for sex determination based on the measured spectrum, shown in FIG. 1, is implemented in a microprocessor that automatically receives the measurement information from the ADC 17. The principal components of the sex determination procedure include outlier detection 102, preprocessing 103, feature extraction 104, and classification 105. The design of each procedure is performed on the basis of a calibration set of exemplary measurements. In this section, the general steps which are detailed in the subsequent Design and Implementation Sections are summarized.

Measurement

Figure 2:
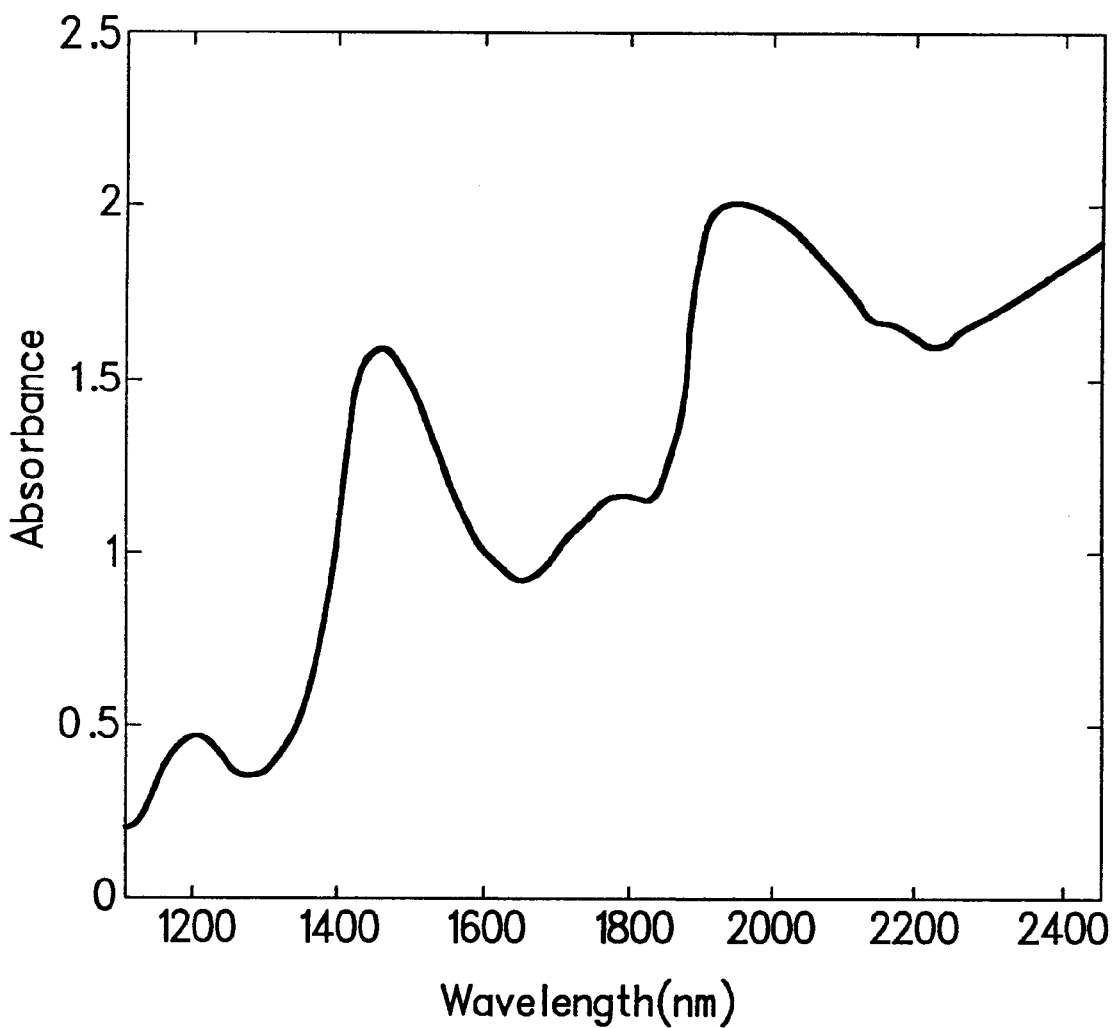
FIG. 2 is a graph plotting a typical noninvasive absorbance spectrum.

The measurement is a spectrum denoted by the vector $m \in \Re^N$ of absorbance values pertaining to a set of N wavelengths $\lambda \in \Re^N$ that span the near infrared (700 to 2500 nm). A typical plot of m versus $\lambda$ is shown in FIG. 2.

Outlier Detection

The outlier detection procedure is a method for detecting invalid measurements through spectral variations that result from problems in the instrument, poor sampling of the subject or a subject outside the calibration set. The preferred method for the detection of spectral outliers is through a principal components analysis and an analysis of the residuals (see H. Martens, T. Naes, *Multivariate Calibration*, John Wiley and Sons, New York, pp. 419 (1989)). First, the spectrum, m, is projected onto five eigenvectors, contained in the matrix o, that were previously developed through a principal components analysis (on a calibration set of exemplary absorbance spectra) and are stored in the computer system of the device. The calculation is given by $$xpc_o = \sum_{k=1}^{7} mo_k \quad (1)$$

and produces the 1 by 5 vector of scores, $xpc_o$ where $o_k$ is the kth column of the matrix o. The residual, q, is determined according to $$q = m - xpc_o o^T \quad (2)$$

and compared to three times the standard deviation of the expected residual (of the a calibration set). If greater, the sample is reported to be an outlier and the sex determination procedure is terminated.

Preprocessing

Preprocessing includes operations such as scaling, normalization, smoothing, derivatives, filtering, and other transformations that attenuate the noise and instrumental variation without affecting the signal of interest. The preprocessed measurement, $x \in \Re^N$, is determined according to $$x = h(\lambda, m) \quad (3)$$

where $h: \Re^{N \times 2} \to \Re^N$ is the preprocessing function.

Feature Extraction

Feature extraction determines the salient characteristics of measurements that are relevant for sex determination. Feature extraction is any mathematical transformation that enhances a quality or aspect of the sample measurement for interpretation. The purpose of feature extraction is to represent concisely and enhance the properties and characteristics of the tissue measurement site for sex determination. In addition, the features provide significant information of the tissue properties they represent and can be used for alternate purposes, such as diagnostics or system optimization.

The features are represented in a vector, $z \in \Re^M$ that is determined from the preprocessed measurement through $$z = f(\lambda, x) \quad (4)$$

where $f: \Re^N \to \Re^M$ is a mapping from the measurement space to the feature space. Decomposing $f(\bullet)$ yields specific transformations, $f_i(\bullet): \Re^N \to \Re^{M_i}$ for determining a specific feature. The dimension, $M_i$, indicates whether the ith feature is a scalar or a vector and the aggregation of all features is the vector z. When a feature is represented as a vector or a pattern, it exhibits a certain structure indicative of an underlying physical phenomenon.

The individual features are divided into two categories: abstract and simple. Abstract features do not necessarily have a specific interpretation related to the physical system. Specifically, the scores of a principal component analysis are useful features although their physical interpretation is not always known (see H. Martens, T. Naes, supra.). For example, the utility of the principal component analysis is related to the nature of the tissue absorbance spectrum. The most significant variation is generally related to the structure which varies systematically with sex. Therefore, the scores of the principal components analysis provides useful information for sex determination and constitute a valuable set of features.

Simple features are derived from an a priori understanding of the sample and can be related directly to a physical phenomenon. For example, the thickness of the dermis or subcutaneous layer, described previously as varying systematically with sex, and result in specific spectral manifestations. These spectral variations are extracted and enhanced and serve as both a feature for sex determination and a measurement of their respective tissue properties.

In the general case, the full spectrum can be passed to the classification system for sex determination. However, the presently preferred embodiment of the invention provides three specific methods of feature extraction that exhibit superior classification performance and measurements of other relevant tissue properties:

1. The scores from factor analysis;
2. Location of critical points on the measured spectrum; and
3. Relative absorption of water and fat.

The detailed implementation of the procedure for extracting these features on the basis of a calibration set is provided in the next section.

Classification

The determination of the subject's sex on the basis of the extracted features is performed through a classification step which involves a mapping and a decision. The mapping step is given by $$L=f(z) \tag{5}$$

where L is a scalar that can be used to measure the distance for the categories of male and female. Generally, two values, $L_{male}$ and $L_{female}$, associated with the representative or mean value of L for the male and female categories respectively are predefined and the class assignment is based on the closeness of L to $L_{male}$ and $L_{female}$. For example, the distance of L to previously established class means classes can be measured by $$d_{male}=|L_{male}-L|$$

$$d_{female}=|L_{female}-L| \tag{6}$$

the decision is made as follows if $d_{male}<d_{female}$ then male
if $d_{male}>d_{female}$ then female The mapping and decision limits are determined from a calibration set of exemplary features and corresponding sexes through a classification calibration procedure. Existing methods include linear discriminant analysis (see R. Duda, P. Hart, *Pattern Classification and Scene Analysis*, John Wiley and Sons, New York (1973)), SIMCA (see S. Wold, M. Sjostrom, *SIMCA: A method for analyzing chemical data in terms of similarity and analogy*, Chemometrics: Theory and Application, ed. B. R. Kowalski, ACS Symposium Series, vol. 52 (1977)), k nearest-neighbor (see R. Duda, P. Hart, supra.), fuzzy classification (see J. Bezdek, S. Pal, eds., *Fuzzy Models for Pattern Recognition*, IEEE Press, Piscataway, N.J. (1992) and J. Keller, M. Gray, J. Givens, *A Fuzzy K nearest Neighbor Algorithm*, IEEE Transactions on Systems, Man, and Cybernetics, Vol. SMC-15, No. 4, pp. 580–585 (July/August, 1985)), and various forms of artificial neural networks (see Y. Pao, *Adaptive Pattern Recognition and Neural Networks*, Addison-Wesley Publishing Company, Inc., Reading, Mass. (1989)).

Implementation Details

This section discloses four specific procedures for sex determination. The structure of the procedures are based on a priori knowledge of the systematic variation of the skin structure, i.e. the variation of skin thickness, amount of subcutaneous fat and collagen structure. However, the parameters of each procedure, such as the eigenvectors for outlier detection, are determined on the basis of a experimental data set providing exemplary information.

Experimental Data Set

A study was performed to generate calibration and validation data for the four procedures disclosed subsequently. Human subjects (266) of diverse age, sex, and ethnicity were recruited at a local health care facility and detailed demographic information about each participant was recorded. Four replicate absorbance spectra were measured on each subject's forearm with the spectrometer described as the preferred embodiment The number of samples per participant was limited to one. The subjects were separated at random into calibration and test sets. The calibration set is employed to construct the models, mappings, and parameters for each of the procedures described below. The validation set was used to test the performance of each procedure for sex determination. The total set of spectra and demographic information shall be referred to as the "Experimental Data Set" in the remainder of the text.

While this is a specific experiment aimed at the determination of a suitable set for calibrating the sex determination apparatus, one can readily appreciate that for different subjects and for different target performance levels other experiments with more or less subjects would be performed.

Method 1—Sex Determination through Spectral Shift

The first method predicts sex based on the spectral shift observed in the measured NIR spectrum. The basis for the method is that systematic sex related differences in the characteristics and properties of the subcutaneous fat and dermis layers causes systematic variation of the absorbance bands of specific analytes, such as fat. However, other background analytes tend to remain constant. The result of the variation in one absorbance band among a particular background is manifested through an apparent shift in the peak and valley locations.

Figure 3:
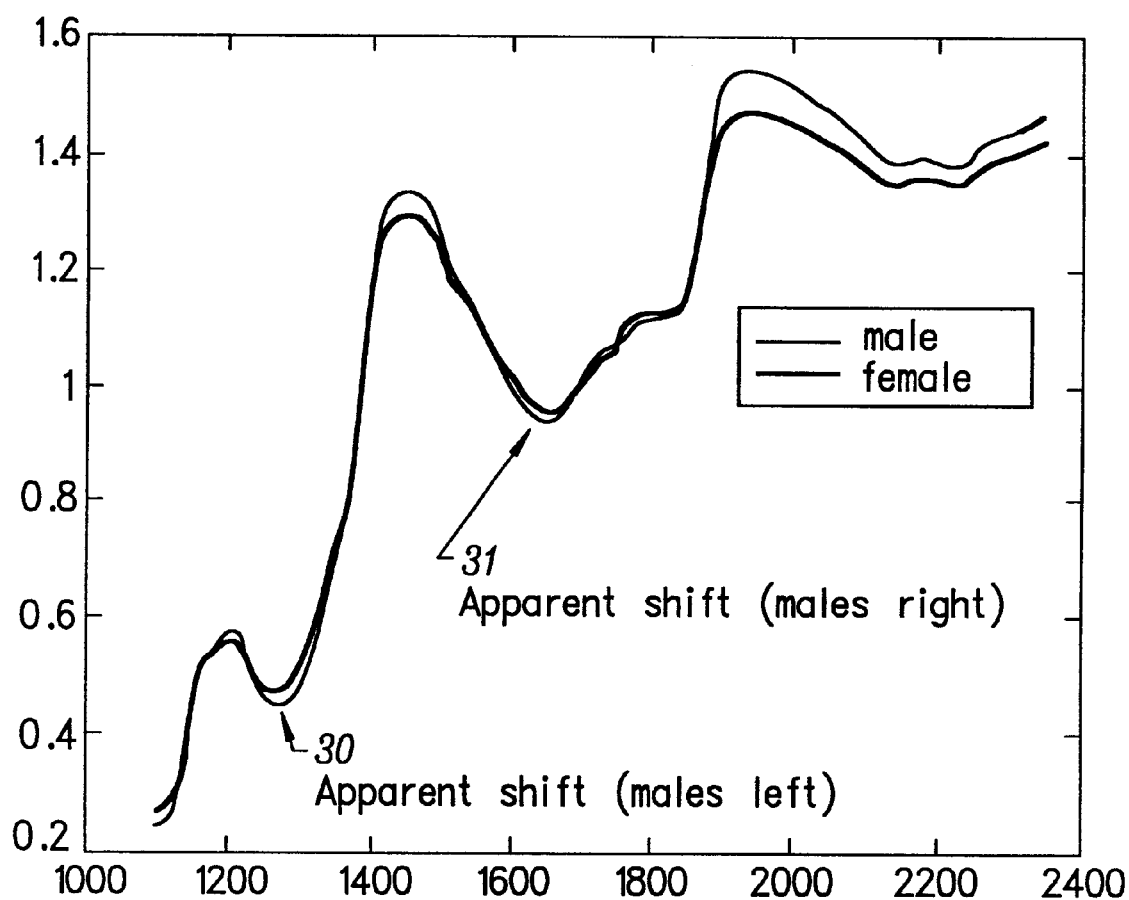
FIG. 3 is a graph plotting NIR spectral measurements and demonstrating spectral shift between male and female subjects.

For example, the spectra of the Experimental Data Set was separated according to sex and averaged. The averaged spectra are depicted in FIG. 3 and show a pronounced difference between the sexes. Specifically, particular peaks and valleys appear shifted between the two sexes as marked on the figure. The wavelength position of the peaks and valleys (the critical points) provide a set of features suitable for determination of sex.

Figure 4:
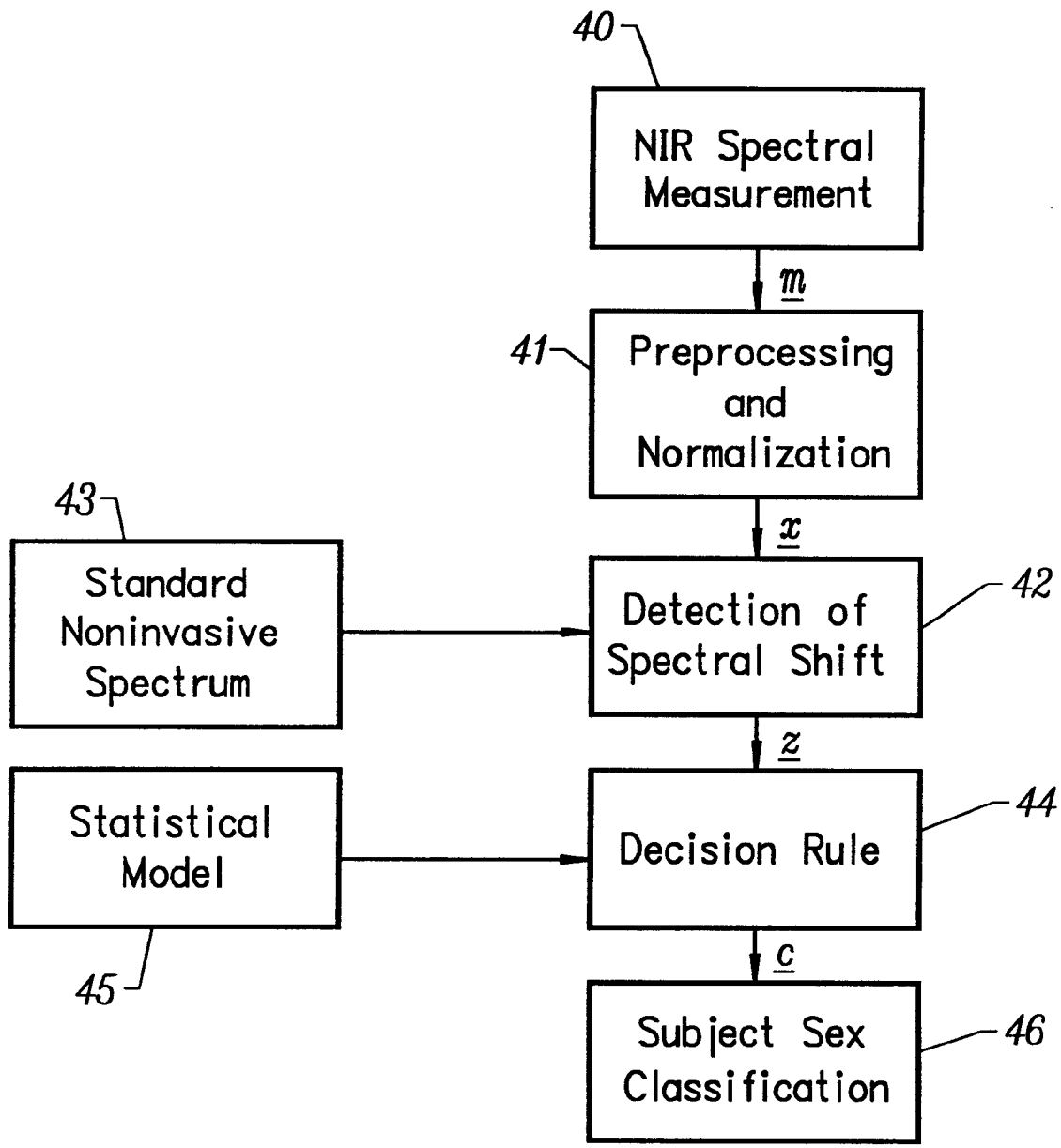
FIG. 4 is a block diagram showing a general procedure for determining individual sex based on the spectral shift of near infrared spectra according to the invention.

The general procedure for utilizing these features is depicted in FIG. 4. First, NIR absorbance spectra are measured 40, such as those shown in FIGS. 2 and 3. The measured spectrum is preprocessed 41 via a 15-point Savisky-Golay smoother in the form of a finite impulse response filter (see A. Savitzky, M. Golay, *Smoothing and Differentiation of Data by Simplified Least Squares Procedures*, Anal. Chem., vol. 36, no. 8, pp. 1627–1639 (1964)). The apparent shift of the measurement at the critical points is measured 42 with reference to a processed standard absorbance spectrum 43. The standard absorbance spectrum can be any single absorbance measurement or the average of a set of measurements. In the preferred embodiment of the invention, the standard absorbance spectrum is the mean of all spectra in the calibration set.

A statistical model 45 is used to identify critical points that are applied using a decision rule 44. The location of the critical points is determined over a finite window in the vicinity of the known critical points (for example, a 10 nm window is used). Locations for critical points that vary according to subject sex include: 1145, 1195, 1230, 1270, 1650, 2160, 2200, 2250, 2305 and 2350 nm. However, the method is general and can be applied to other spectral regions. In addition, other critical points can be easily selected from the first or second derivative of the absorbance spectrum.

The wavelength position of each critical point is determined by fitting a second-order polynomial function to the measured spectrum in the vicinity of the known critical point locations, determining the derivative of the polynomial, and calculating the root. For example, given the polynomial $$\hat{y}=a+bx+cx^2 \tag{7}$$

where x is the wavelength and $\hat{y}$ is the estimated absorbance in the vicinity of a critical point. The parameters a, b and c are calculated through standard regression techniques between x and y, the measured absorbance spectrum. The estimated peak location, p, is given by $$p = \frac{b}{2c}. \quad (8)$$

Alternate methods of determining the critical point can also be used, such as zero-crossing algorithms, gradient search algorithms, or methods based on a cross-correlation function between the standard and measurement spectra.

Given a calibration set of spectra, the spectral features (critical points) are extracted as described above and linear discriminant analysis or Mahalanobis distance is used to determine the classification model 44 (see R. Duda, P. Hart, supra.). For example, the Mahalanobis distance of a set of critical points associated with a measured spectrum is given by $$d_{male} = (p - p_{male})S^{-1}(p - p_{male})$$

$$d_{female} = (p - p_{female})S^{-1}(p - p_{female}) \quad (9)$$

were p is the vector of critical points, $p_{male}$ is the mean of the critical point locations over all males in the calibration set, $p_{female}$ is the mean of the critical point locations over all females in the calibration set, S is the covariance of the critical points over the calibration set and $d_{male}$ and $d_{female}$ correspond to the closeness of the critical point to the male and female class represented by the calibration set. The same critical points are calculated for future spectral measurements and Equation 9 is applied to determine the sex of the subject.

For classification using a single critical point, the squared statistical distance is calculated and used to determine the sex of the subject through the calculation $$d^2_{male} = \left(\frac{p - p_{male}}{s_{male}}\right)^2 \quad (10)$$

$$d^2_{female} = \left(\frac{p - p_{female}}{s_{female}}\right)^2$$

where p is the location of the critical point, $p_{male}$ and $s_{male}$ are the mean and standard deviation of the critical point locations over all males in the calibration set, $p_{female}$ and $s_{female}$ are the mean and standard deviation of the critical point locations over all females in the calibration set and $d_{male}$ and $d_{female}$ correspond to the closeness of the critical point to the male and female class represented by the calibration set.

Given the distances calculated in Equations (9) or (10), the sex is determined 46 (FIG. 4) through if $d_{male} < d_{female}$ then male
if $d_{male} > d_{female}$ then female The same critical points are calculated for future spectral measurements and Equation 9 or 10 is applied with these decision rules to determine the sex of the subject.

Figure 5:
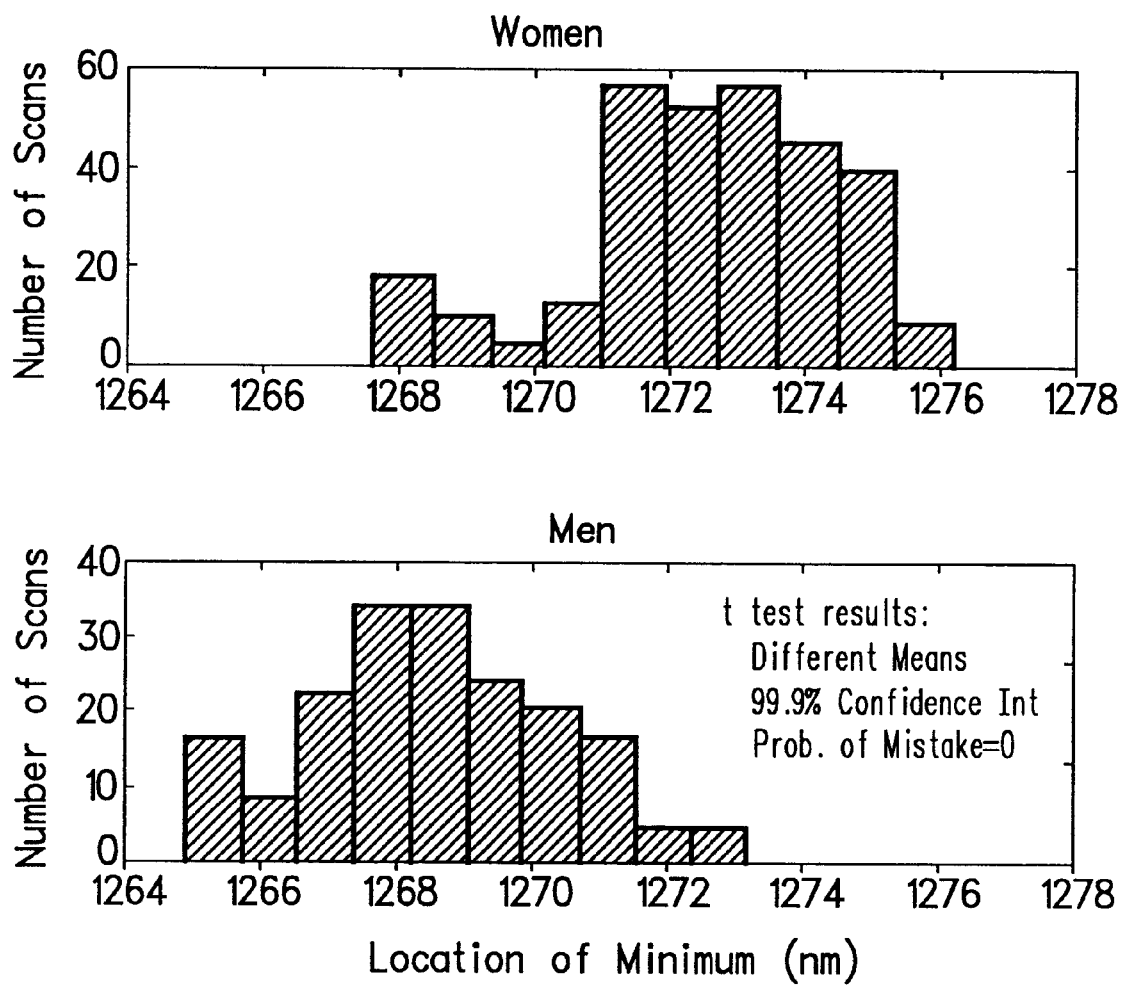
FIG. 5 provides histograms of the spectral minimum near 1270 nm separated by sex.
Figure 6:
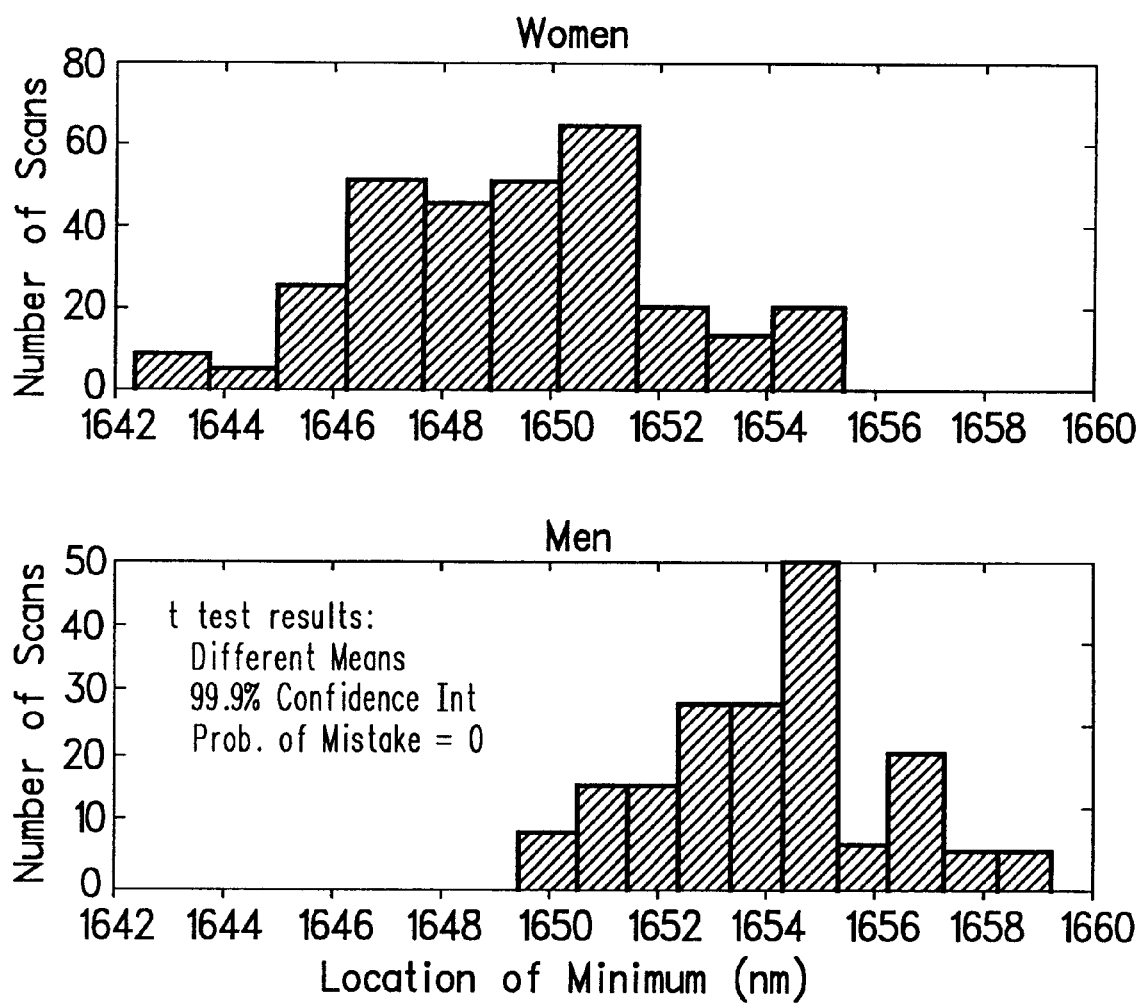
FIG. 6 provides histograms of the spectral minimum near 1650 nm separated by sex.
Figure 7:
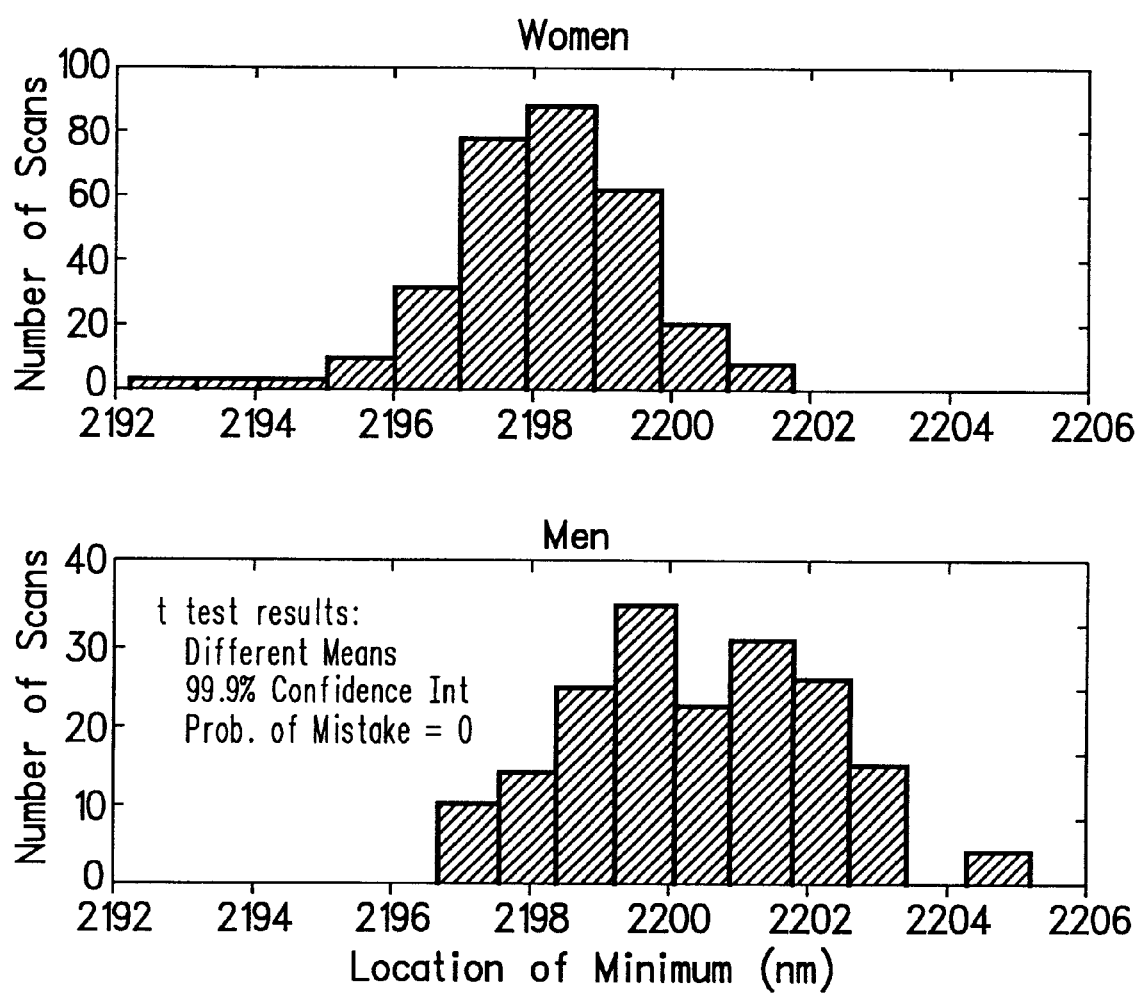
FIG. 7 provides histograms of the spectral minimum near 2200 nm separated by sex.

As an example, the procedure for sex determination was applied to the calibration and test sets comprising the Experimental Data Set. First, the critical points were determined at the following wavelengths 1270, 1650, and 2200 nm. The calculated critical points for the each sample of the Experimental Data Set are plotted via histograms in FIGS. 5–7. The figures show that the locations of the critical points are normally distributed about a mean level. However, this mean is systematically different between males and females. The determination of sex is possible through the process outlined above and produced validation set results on the Experimental Data Set with a sex determination accuracy of 85%. The use of additional critical points further improves the performance, while fewer critical points afford simpler procedures but degrade performance.

Furthermore, the various critical points shown provide an indication of the thickness of the dermis, subcutaneous tissue and the properties of the dermis. For example, the points at 1270 nm vary primarily according to the thickness of the subcutaneous fat due to the deeper penetration of the NIR energy. The critical point at 1650 can be used to provide relative information about the thickness of the dermis and the critical point at 2200 nm is likely related to the properties of collagen fibers in the dermis. This information can be used to further classify the subjects for blood analyte prediction, analysis of body composition or determination of environmental influences on skin properties.

Method 2—Sex Determination through Abstract Feature Extraction

Figure 8:
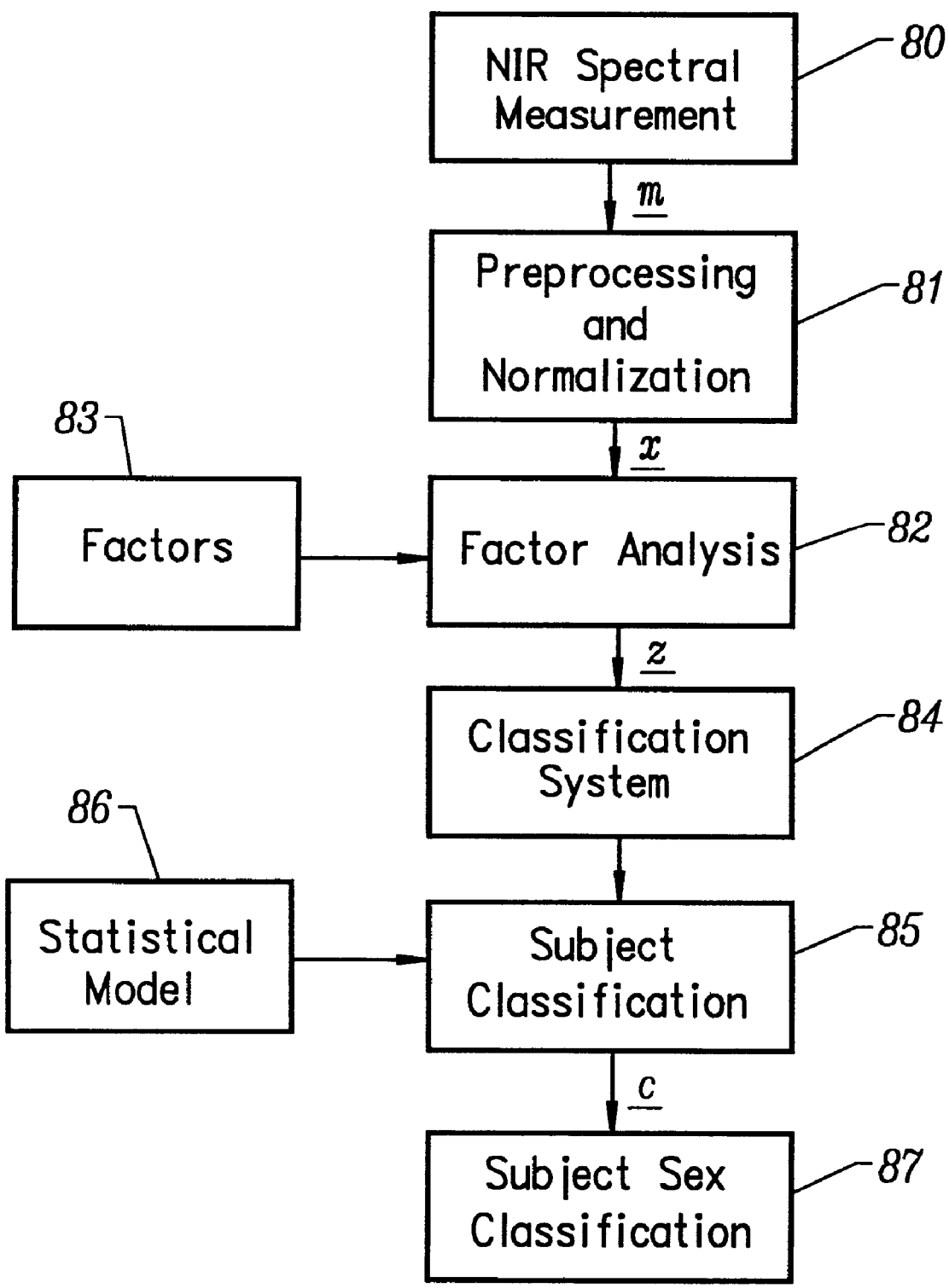
FIG. 8 is a block schematic diagram of a classification system for determining the sex of a subject based on an NIR measurement according to the invention.

The second method, illustrated in FIG. 8, is distinguished by the use of factor analysis to develop a set of abstract features capable of representing the spectral variation related to sex. The measurement is a NIR absorbance spectrum 80 similar to that shown on FIG. 2. The spectrum is sub-divided into one or more regions according to wavelength (wavelength selection) and is preprocessed and normalized 81 to enhance spectral variation related to sex. The measurements are projected 82 onto one or more sets of previously determined factors (eigenvectors) 83 to determine the scores. The scores are the extracted features and are subjected to a classification procedure 84–87, such as linear discriminant analysis, SIMCA, k nearest-neighbor and various forms of artificial neural networks to predict the sex of the subject.

EXAMPLE 1
Human Subject Sex Determination

As an example the Experimental Data Set was analyzed to demonstrate the utility of abstract features. First, wavelength selection was applied to reduce the spectra to the 1100–1400 nm range. An 11-point Savisky-Golay smoother was applied and the set of spectra were subjected to multiplicative scatter correction, as described below. A principal components analysis was performed and the scores of the first three eigenvectors were calculated and are plotted in FIG. 9 (90, 92, 94) according to sex. The scores, representing variation in the spectra, show a pronounced systematic separation according to subject's sex.

Figure 10:
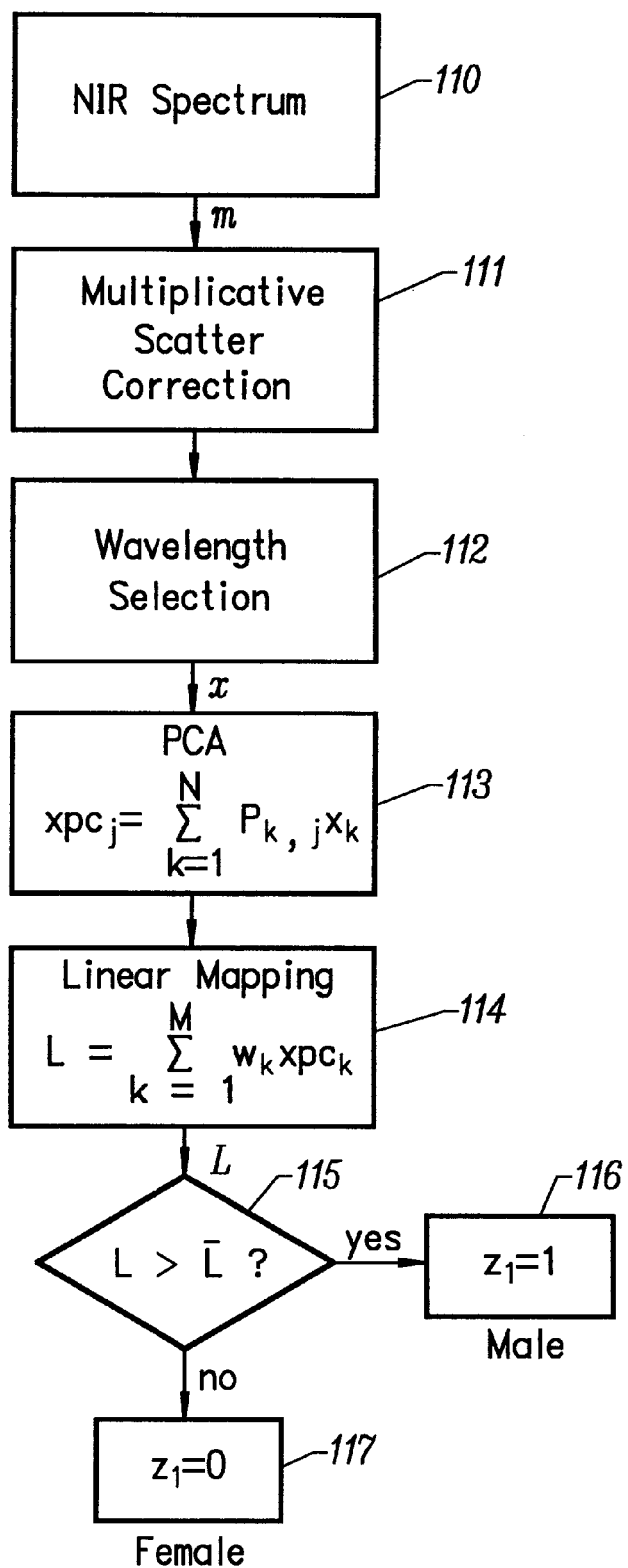
FIG. 10 is a block schematic diagram of a procedure for sex determination through abstract features and linear classification according to the invention.

The preferred embodiment of the sex determination (through the abstract feature extraction) procedure is shown in FIG. 10 and involves spectral preprocessing 110–112, decomposition through principal components analysis 113, and classification through linear discriminant analysis 114–117.

First, the absorbance spectrum, m, is provided from the outlier detection system 110. Wavelength selection 112 is applied to truncate the spectral range to regions with significant absorption due to fat in adipose tissue (1100 to 1400 nm). The spectrum is also processed through multivariate scatter correction 111 (see P. Geladi, D. McDougal, H. Martens, *Linearization and Scatter-Correction for Near-Infrared Reflectance Spectra of Meat*, Applied Spectroscopy, vol. 39, pp. 491–500 (1985)) through a rotation that fits it to the expected or reference spectrum, $\bar{m}$, determined from the calibration set. First, the spectrum is fit via linear regression according to $$m = a + b\tilde{m} + e \qquad (11)$$

where a and b are the slope and intercept and e is the error in the fit. The spectrum is then corrected through $$x = \frac{(m-a)}{b} \qquad (12)$$

where x is the processed absorbance spectrum. The processed spectrum is projected onto the eigenvectors, $p_k$, that were previously developed through a principal components analysis (on the calibration set) 113. The calculation, shown in FIG. 10, produces the 1 by N vector of scores, xpc.

A discriminant function is applied to classify the subjects on the basis of the first M scores (M=5 is this application). The scores are rotated through a cross product with the discriminant, w, as depicted in FIG. 10 to produce the scalar, L 114. This result is compared to $\overline{L}$, the center between the two classes 115. If L>$\overline{L}$ then the subject is classified as a female 117. If not, the spectrum is classified as beloning to a male 116.

This system was implemented with five factors selected and the mean spectrum for MSC, the eigenvectors (p) and discriminant function (w) shown, were calculated using the calibration set. Application of the procedure to determine the sex of the validation set resulted in a 90% correct sex determination accuracy.

The method of classification described above can be replaced by other more suitable techniques depending on the resource and performance requirements. For example, the Fuzzy-K nearest neighbor classification algorithm reported by Keller (see J. Keller, M. Gray, J. Givens, supra.) was applied with 15 neighbors in place of the discriminant analysis discussed above. The method resulted in a validation set accuracy of 93%.

Figure 9:
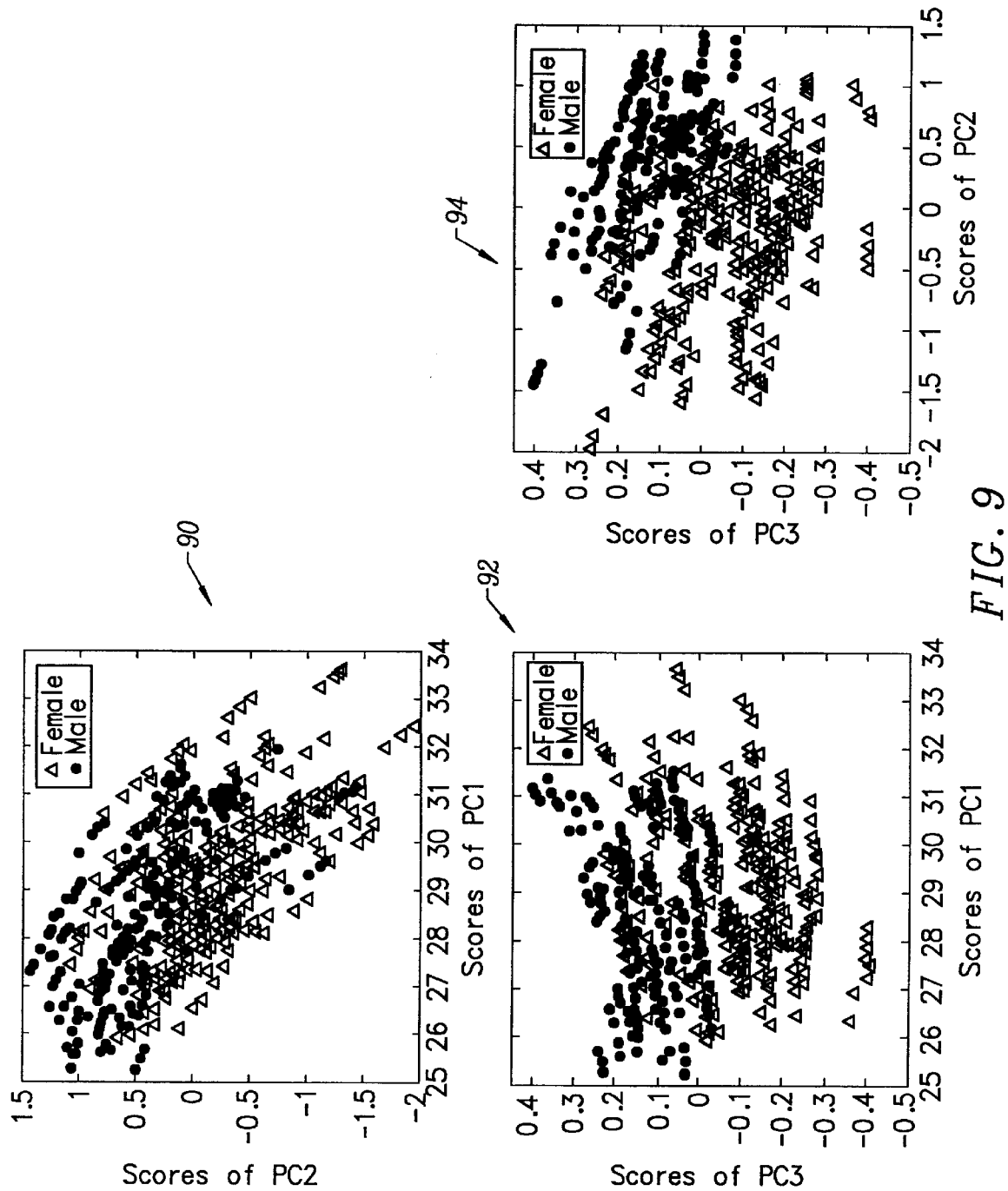
FIG. 9 provides plots of the scores from NIR spectral regions illustrating the separation of abstraction features related to sex.
Figure 11:
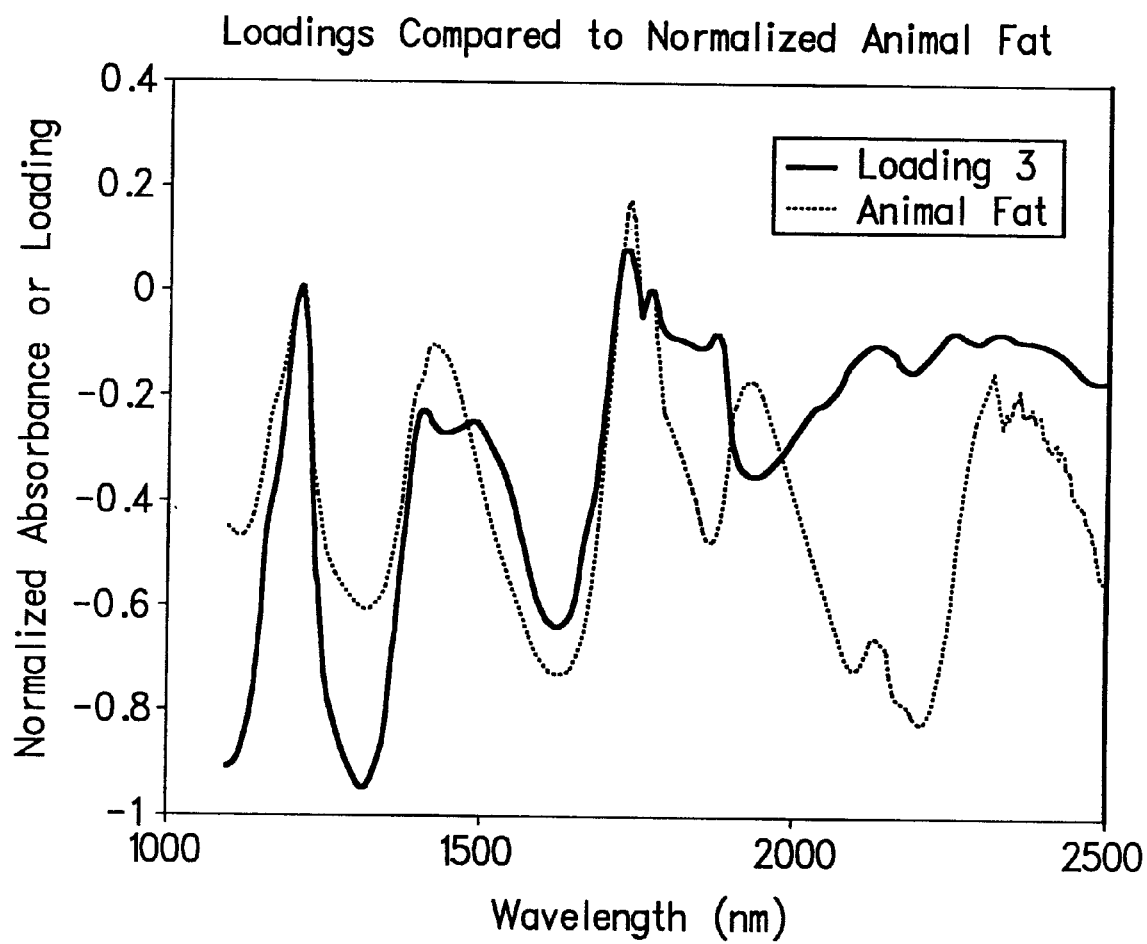
FIG. 11 is a graph showing loading of the third principal component compared to the absorbance spectrum of animal fat.

Further, the scores of the abstract factors provide relative information regarding the thickness of the subcutaneous fat, the dermis, and the level of collagen density in the dermis. For example, the factor corresponding to the third principal component of FIG. 9 is plotted in FIG. 11 along with the pure component spectrum of animal (bovine) fat. The correspondence of the major fat absorbance bands between the two features indicates that the scores of the third factor represent the absorbance due to fat manifested in the measured spectra. The differences between the factor and the fat spectrum are caused by the covariation of other interferents and differences in the mode of measurement.

EXAMPLE 2

Sex Determination of Mice

Sex Determination through Abstract Feature Extraction was implemented for the determination of the sex of genetically altered growth hormone mouse. Growth hormone transgenic mice have foreign growth hormone genes introduced into their genome under the control of a promoter. The introduction of foreign growth hormone genes into their genome causes the animal continually to produce excessive amounts of growth hormone (see R. Wanke, E. Wolf, W. Hermanns, S. Folger, T. Buchmuller, G. Brem, *The GH-Transgenic Mouse as an Experimental Model for Growth Research: Clinical and Pathological Studies*, Hormone Research, vol. 37, pp. 74–87(1992)).

Figure 12:
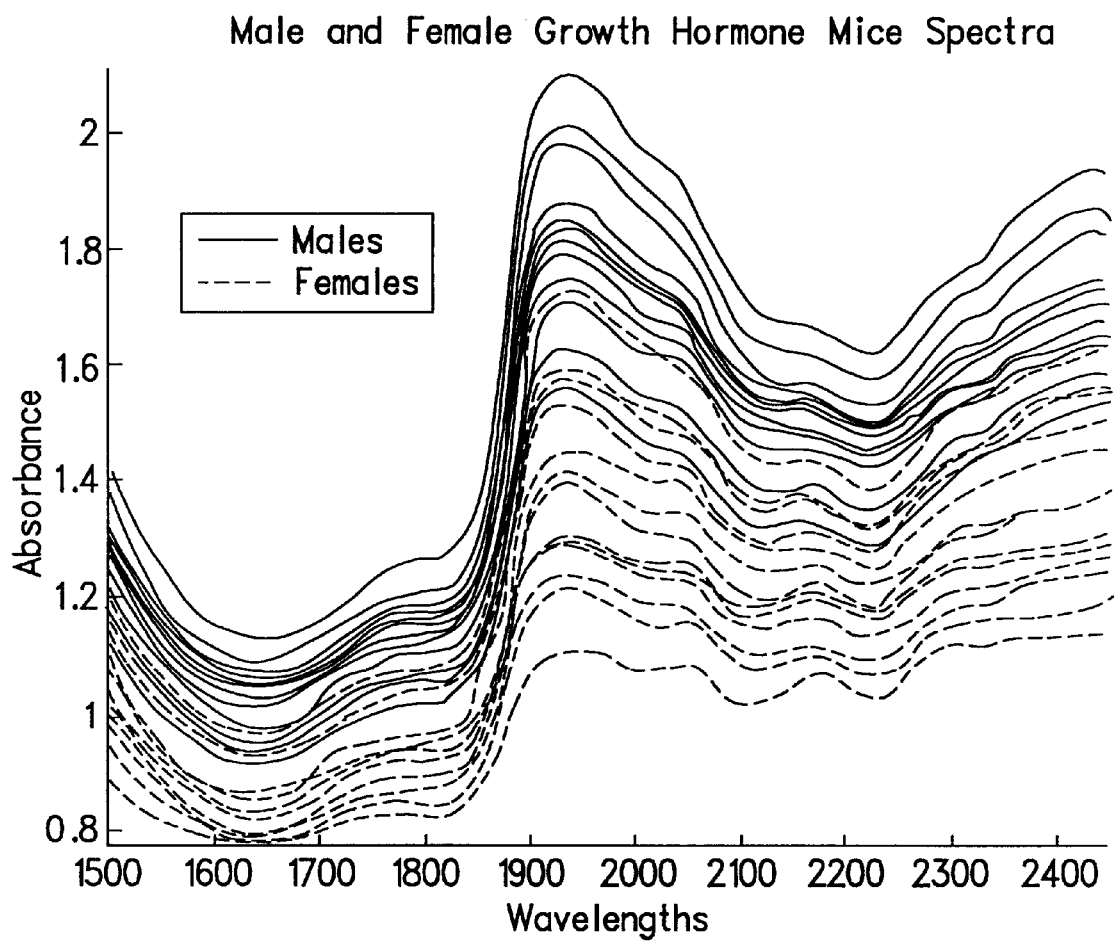
FIG. 12 is a graph showing NIR measurements from growth hormone mice using a spectrometer.

Spectral data was collected on a diffuse reflection spectrometer from fourteen growth hormone mice in the wavelength range 1100–2400 nm. The belly of the mouse was scanned and the intensity spectra were converted to absorbance as described previously. A plot of the resulting absorbances by sex revealed an overall higher absorbance across all wavelengths on female mice as compared to male mice (FIG. 12). Based on the plot, wavelength selection was performed and the spectra were narrowed to 1500 to 2450 nm.

Figure 13:
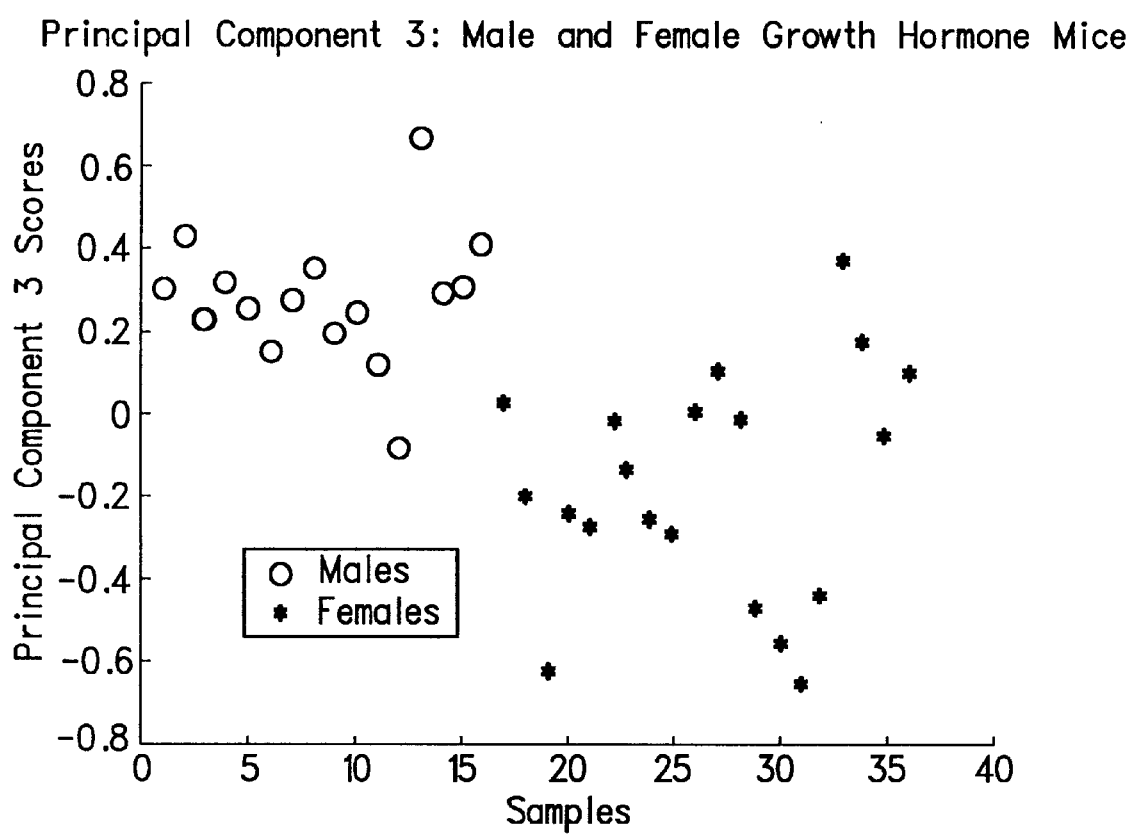
FIG. 13 is a plot showing separation by gender in principal component three scores.
Figure 14:
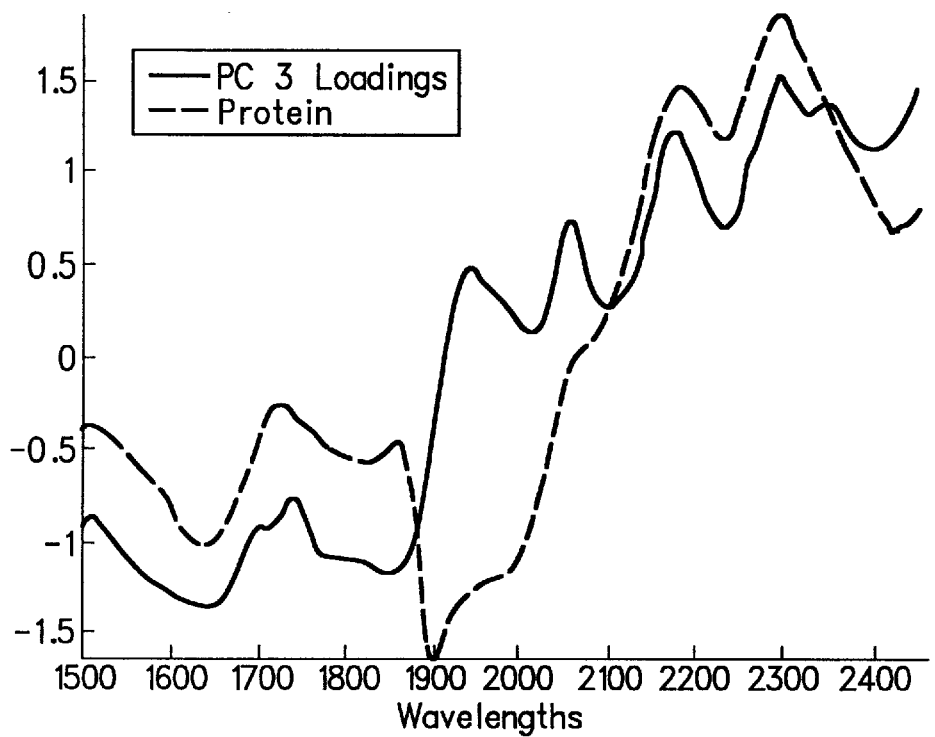
FIG. 14 is a plot showing a comparison of principal component three loading to a protein spectrum.
Figure 15:
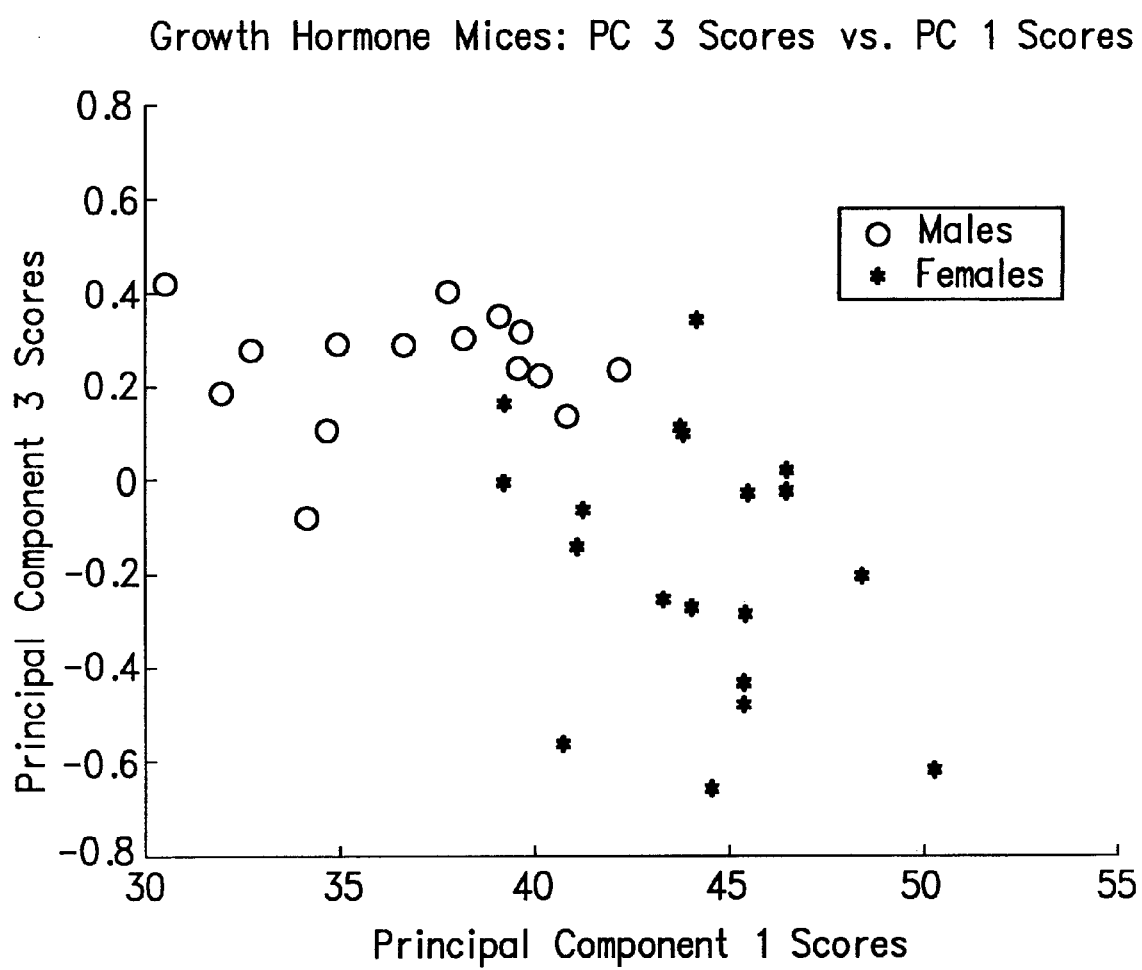
FIG. 15 is a plot showing a principal component three versus principal component one scores.

Principal component analysis (PCA) was performed on the selected wavelength region (1500 to 2450 nm) of the growth hormone mouse data. The first three principal components were found to be significant through inspection of the factor scores. Principal component three scores separate into two groups according to sex (FIG. 13). Principal component three loadings resemble protein spectrum (FIG. 14). This indicates the difference between the mouse sexes are related to variations in the protein content of the mouse tissue. The mice cluster into two groups corresponding to sex by plotting principal component one scores against principal component three scores (FIG. 15).

Linear discriminant analysis, described above, was applied to the first three principal components scores. Sex determination performance was evaluated through cross-validation using the "leave-one-out" strategy and calculating the percent prediction error. The cross-validation procedure is used iteratively to predict the mouse sex by using all other samples to construct the calibration model (see H. Martens, T. Naes, supra.). Using this technique, the growth hormone mice were correctly classified with 88% test accuracy (see Table 1).

TABLE 1

| Gender Classification Results | |
|---|---|
| Classification Variable | GH Mice |
| Number of Classes | 2 |
| Number of Correct Classifications | 32 |
| Number of Misclassifications | 4 |
| Percent Correctly Classified | 89 |
| Percent Error | 11 |

| Results from Classification | | | |
|---|---|---|---|
| Class | Misclassified | Correct | Total |
| 1 | 2 | 14 | 16 |
| 2 | 2 | 18 | 20 |

Therefore, the growth hormone mice can be classified according to gender by differences in the structural and chemical composition of the protein in their tissue. Further, the systematic differences in sex are modeled by absorption features corresponding to protein. Therefore, the abstract features provide quantitative and relative information about the significant properties of mice tissue related to sex.

Method 3—Sex Determination through Projection of a Basis Set

The third method involves the projection of a basis set of pure component spectra onto the measured noninvasive absorbance spectrum to generate key features. The procedure, depicted in FIG. 16, involves the preprocessing and wavelength selection of the measured absorbance spectrum 160. A basis set of pure component spectra 161 is projected onto the measured spectrum 162, as shown in the figure. The basis set is comprised of the key constituents, such as water, fat, and protein, which are related to the systematic spectral variation caused by the sex of the subject. In the figure, the absorbance spectra of water and fat are used to create the 2 by M vector, p, comprising the basis set. However, additional analyte spectra can be added for additional information or accuracy, for example protein.

The basis set is fit to the measured spectrum, as shown in the figure, and produces the 1 by 2 vector of weights, m. The weights are representative of the absorbance due to water or fat and provide relative information about the thickness of the dermis (in the case of the magnitude of water) and the amount of subcutaneous fat (in the case of the magnitude of fat) 163. This information can be used for characterizing the subject, body composition assessment, or for diagnostic purposes 164.

A discriminant function 165 is applied to classify the subjects based on the two features contained in m through the equation shown in the figure to produce the scalar, L. This result is compared to $\bar{L}$, the center between the two classes 166. If L>$\bar{L}$ then the subject is classified as a female 167. If not, the spectrum is classified as beloning to a male 168.

Figure 16:
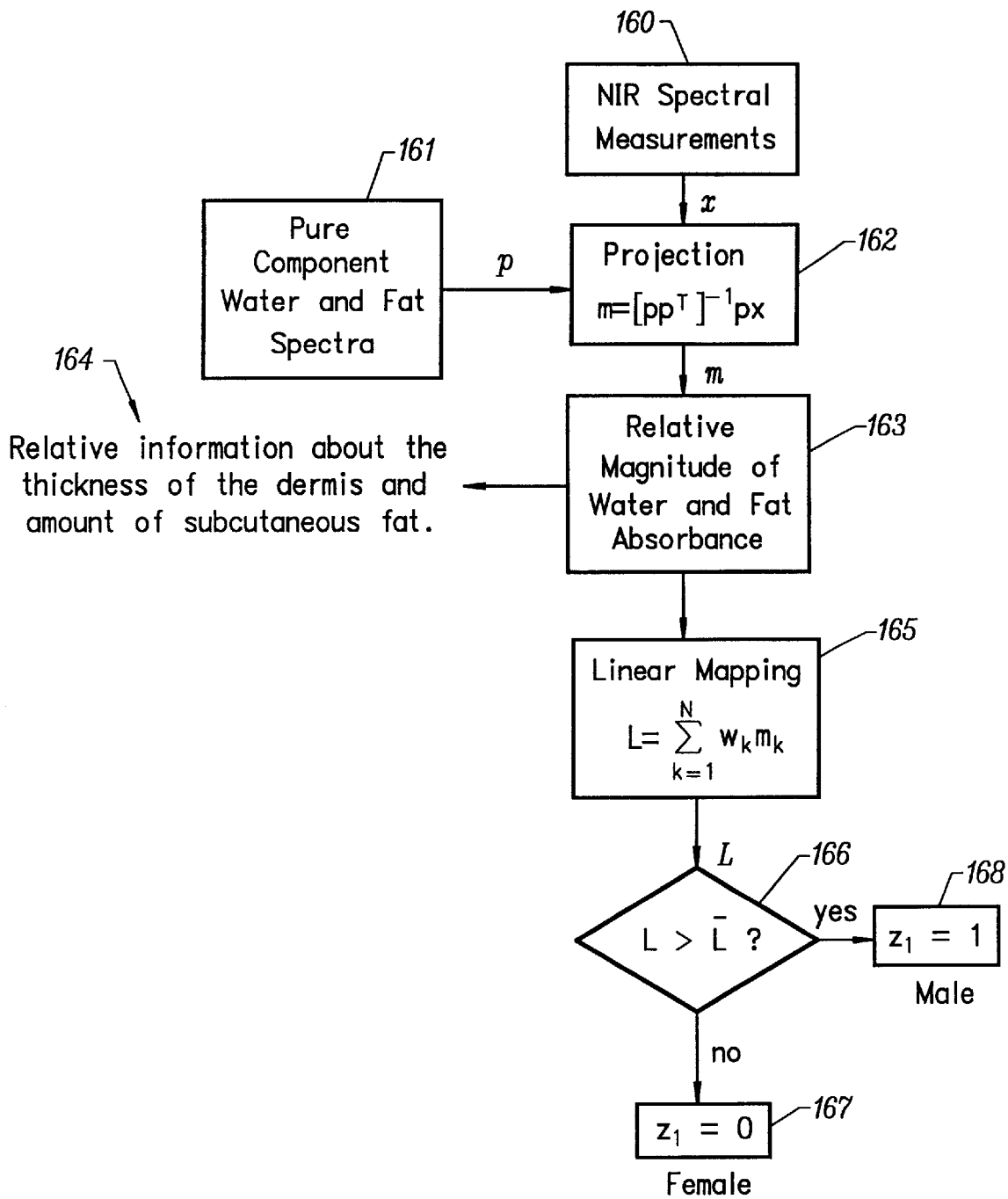
FIG. 16 is a block schematic diagram showing a procedure for sex determination on the basis of feature extraction through pure component absorbance spectra of water and fat according to the invention.
Figure 17:
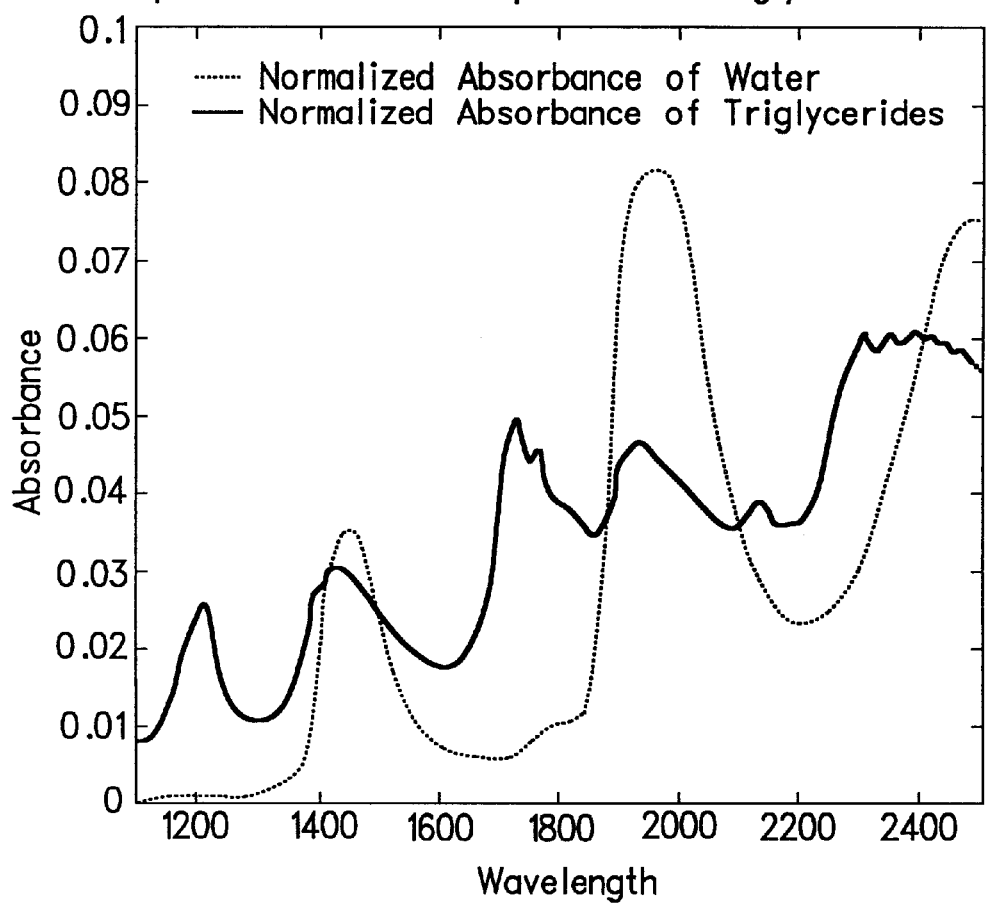
FIG. 17 is a graph showing pure component absorbance spectra of water and triglycerides (fat)
Figure 18:
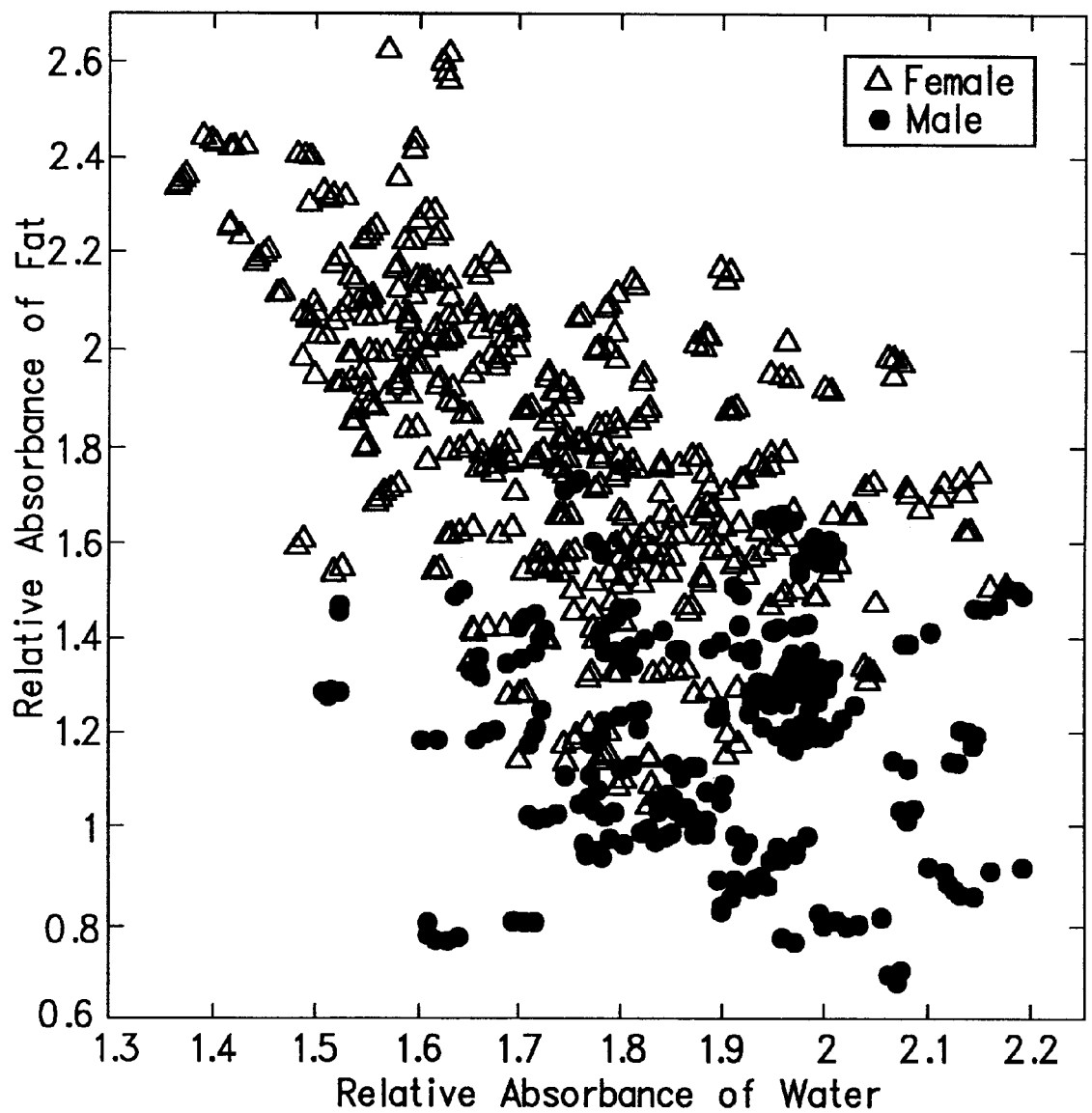
FIG. 18 is a plot showing the extracted features related to the absorbance of fat and water separated by sex.

As an example, the pure component spectra shown in FIG. 17 of fat and water were normalized to unit length and applied to the Experimental Data Set according to the procedure in FIG. 16. The wavelength regions were limited to 1100–1350 nm and the relative magnitude of water and fat that was produced by projecting the basis set onto each absorbance spectrum in shown in FIG. 18. As FIG. 18 indicates, the absorbance of water is higher in males than in females. Since the absorbance in the dermis is primarily due to the concentration of water, and the concentration of water is within a limited range between subjects, the relative magnitude of water indicates the pathlength through the dermis. This is consistent with published reports that the dermis of males is thicker than the dermis of females (see C. Tan, B. Statham, R. Marks, P. Payne, supra.). In addition, the magnitude of fat is systematically higher in females than males indicating greater absorbance due to the fat in subcutaneous tissue. Further, this general procedure can be used to extract any specific characteristic that distinguishable by a unique or dominant absorber.

Using the calibration set, the linear mapping of FIG. 16 was developed via linear discriminant analysis (see R. Duda, P. Hart, supra.) and produced the following weight vector $$w=[-0.559 \; 0.9982] \quad (13)$$

From the calibration set, the mean value for L was found to be 1.51. Using these parameters in conjunction with FIG. 18 produced a sex prediction accuracy in the validation set of 87%.

Method 4

Figure 19:
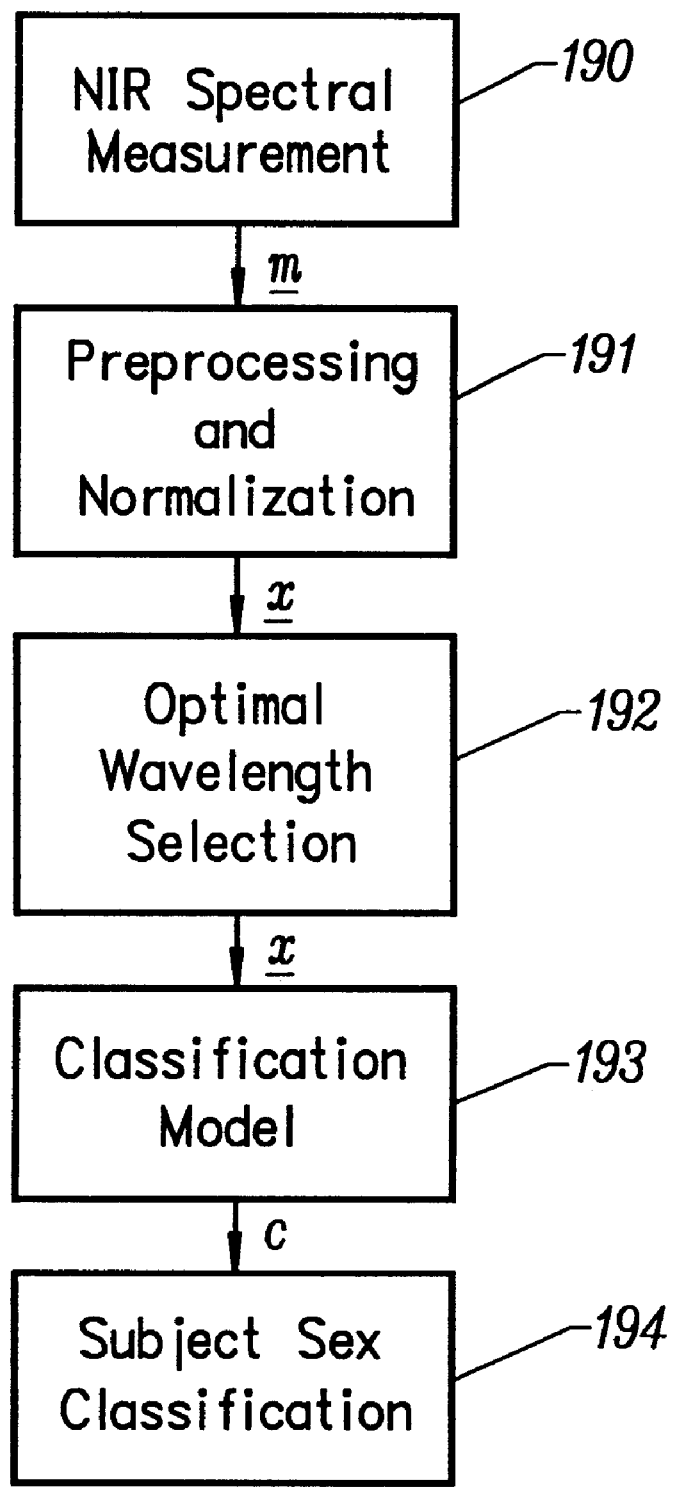
FIG. 19 is a block schematic diagram of a classification of subject sex based on NIR spectral measurements through optimal wavelength selection and a global model according to the invention.

The final method disclosed (see FIG. 19) uses a general linear or nonlinear mapping to directly determine the sex of the subject. The NIR spectral measurement 190 is subjected to preprocessing and normalization 191 to reduce background interference and enhance variation related to sex. The key wavelength regions related to sex are extracted 192, which include the first and second overtone regions (1100–1800 nm), and provided to a classification model 193. The model is a linear or nonlinear mapping which produces the subject sex classification 194 directly.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A method for determining the sex of animal and/or human subjects based on NIR measurements of a skin tissue, comprising the steps of:

measuring tissue properties and characteristics that are manifested spectrally and that vary systematically according to said subject's sex;

applying a calibration model that is empirically derived from a set of exemplary samples consisting of tissue measurements and the actual sex of a population of subjects; and determining said subject's sex.

2. The method of claim 1, wherein said measuring step comprises the step of:

using a spectroscopic apparatus in conjunction with an optical interface.

3. The method of claim 1, wherein said measurements are made in a spectrum denoted by the vector m$\in\Re^N$ of absorbance values pertaining to a set of N wavelengths $\lambda\in\Re^N$ that span the near infrared (700 to 2500 nm).

4. The method of claim 1, wherein said method further comprises the step of:

determining tissue properties of a sampled tissue volume.

5. The method of claim 4, wherein said properties comprise any of thickness of the dermis, collagen content, skin density, and the amount of subcutaneous fat at a measurement site.

6. The method of claim 1, wherein said determining step further comprises any of the steps of:

performing an outlier detection step to detect invalid measurements through spectral variations that result from any of the following problems in the instrument, poor sampling of the subject, and a subject outside the calibration set;

performing a preprocessing step;

performing a feature extraction step to represent concisely and enhance the properties and characteristics of a tissue measurement site for sex determination; and performing a classification step.

7. The method of claim 6, wherein said outlier detection step comprises the step of:

performing a principal components analysis and an analysis of the residuals.

8. The method of claim 6, wherein said preprocessing step comprises the step of: performing transformations that attenuate the noise and instrumental variation without affecting the signal of interest.

9. The method of claim 8, wherein said step of performing transformations comprises any of the steps of performing scaling, normalization, smoothing, derivatives and filtering.

10. The method of claim 6, wherein said feature extraction step comprises the step of:

applying a mathematical transformation to enhance a quality and/or aspect of a sample measurement for interpretation.

11. The method of claim 10, wherein said mathematical transformation comprises any of:

a scores from factor analysis;

location of critical points on a measured spectrum; and a determination of relative absorption of water and fat.

12. The method of claim 6, wherein said classification step comprises the steps of:

performing a mapping; and making a decision.

13. The method of claim 12, wherein mapping and decision limits are determined from a calibration set of exemplary features and corresponding sexes through a classification calibration procedure.

14. The method of claim 13, wherein said calibration procedure comprises any of linear discriminant analysis, k nearest-neighbor, fuzzy classification, and the use of artificial neural networks.

15. A method for determining the sex of animal and/or human subjects based on measurements of a skin tissue, comprising the steps of:

measuring an NIR spectrum of said subject's skin tissue; and predicting sex based on spectral shift observed in said measured NIR spectrum;

wherein systematic sex related differences in characteristics and properties of said subject's subcutaneous fat and dermis layers causes systematic variation of absorbance bands of specific analytes while other background analytes tend to remain constant; and wherein variation in one absorbance band among a particular background is manifested through an apparent shift in peak and valley locations.

16. The method of claim 15, further comprising the step of:

preprocessing said measured spectrum via a 15-point Savisky-Golay smoother in the form of a finite impulse response filter.

17. The method of claim 16, further comprising the step of:

measuring an apparent shift at a critical points with reference to a processed standard absorbance spectrum.

18. The method of claim 17, further comprising the step of:

using a statistical model to identify critical points that are applied using a decision rule, wherein a location of said critical points is determined over a finite window in the vicinity of known critical points and wherein locations for critical points that vary according to subject sex.

19. The method of claim 18, further comprising the steps of:

determining a wavelength position of each critical point by fitting a second-order polynomial function to the measured spectrum in the vicinity of said known critical point locations;

determining a derivative of said polynomial; and calculating a root.

20. The method of claim 19, further comprising the step of:

extracting spectral features.

21. The method of claim 20, further comprising the step of:

using linear discriminant analysis or Mahalanobis distance to determine a classification model.

22. A method for determining the sex of animal and/or human subjects based on measurements of a skin tissue, comprising the steps of:

measuring an NIR spectrum of said subject's skin tissue; and using factor analysis to develop a set of abstract features capable of representing the spectral variation related to sex.

23. The method of claim 21, further comprising the steps of:

sub-dividing said spectrum into one or more regions according to wavelength (wavelength selection);

preprocessing said regions; and normalizing said regions to enhance spectral variation related to sex.

24. The method of claim 23, further comprising the step of:

projecting measurements of said regions onto one or more sets of previously determined factors to determine scores, wherein said scores are extracted features.

25. The method of claim 24, further comprising the step of:

subjecting said scores to a classification procedure that, optionally, comprises any of linear discriminant analysis, SIMCA, k nearest-neighbor, and a form of artificial neural networks, to predict the sex of the subject.

26. The method of claim 25, further comprising the steps of:

spectral preprocessing;

decomposition through principal components analysis; and classification through linear discriminant analysis.

27. A method for determining the sex of animal and/or human subjects based on measurements of a skin tissue, comprising the steps of:

measuring an NIR spectrum of said subject's skin tissue; and projecting a basis set of pure component spectra onto a measured noninvasive absorbance spectrum to generate key features.

28. The method of claim 27, further comprising the step of:

preprocessing and wavelength selection of said measured spectrum.

29. The method of claim 27, wherein said basis set is comprised of key constituents which are related to the systematic spectral variation caused by the sex of a subject.

30. The method of claim 27, further comprising the step of:

applying a discriminant function to classify subjects.

31. A method for determining the sex of animal and/or human subjects based on measurements of a skin tissue, comprising the steps of:

measuring an NIR spectrum of said subject's skin tissue; and using either of a general linear or nonlinear mapping to directly determine the sex of a subject.

32. The method of claim 31, further comprising the step of:

subjecting said NIR spectral measurement to preprocessing and normalization to reduce background interference and enhance variation related to sex.

33. An apparatus for determining the sex of animal and/or human subjects based on NIR measurements of skin tissue, comprising:

means for measuring tissue properties and characteristics that are manifested spectrally and that vary systematically according to said subject's sex;

means for applying a calibration model that is empirically derived from a set of exemplary samples consisting of tissue measurements and the actual sex of a population of subjects; and means for determining said subject's sex.

* * * * *